United States Patent
Fischer et al.

(10) Patent No.: US 6,974,827 B2
(45) Date of Patent: Dec. 13, 2005

(54) PHENYL SUBSTITUTED 4-HYDROXY TETRAHYDROXYPYRIDONE

(75) Inventors: Reiner Fischer, Monheim (DE); Alan Graff, Leverkusen (DE); Axel Trautwein, Bergisch Gladbach (DE); Astrid Ullmann, Köln (DE); Udo Schneider, Leverkusen (DE); Ralf Wischnat, Köln (DE); Mark Wilhelm Drewes, Langenfeld (DE); Christoph Erdelen, Leichlingen (DE); Dieter Feucht, Monheim (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/257,237

(22) PCT Filed: Apr. 5, 2001

(86) PCT No.: PCT/EP01/03864
§ 371 (c)(1),
(2), (4) Date: Oct. 9, 2002

(87) PCT Pub. No.: WO01/79204
PCT Pub. Date: Oct. 25, 2001

(65) Prior Publication Data
US 2003/0176464 A1 Sep. 18, 2003

(30) Foreign Application Priority Data
Apr. 18, 2000 (DE) .......................... 100 19 145

(51) Int. Cl.[7] .................. A01N 43/40; C07D 211/74
(52) U.S. Cl. ........................................ 514/348; 546/296
(58) Field of Search .......................... 546/296; 514/348

(56) References Cited

FOREIGN PATENT DOCUMENTS

| JP | 11-152273 | * | 8/1999 |
| WO | 01/17972 | * | 3/2001 |

OTHER PUBLICATIONS

Damhardt et al, "Anti–mycobacterial 4–hydroxy etc" Eur. J. Med. Chem. (1991) 26, 599–604.*

* cited by examiner

Primary Examiner—Patricia L. Morris
(74) Attorney, Agent, or Firm—Richard E. L. Henderson

(57) ABSTRACT

The present invention relates to novel compounds of the formula (I)

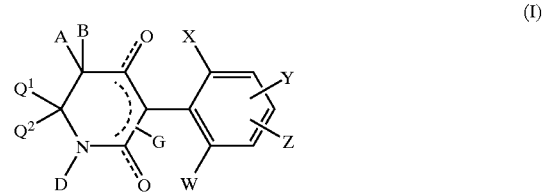

in which
W, X, Y, Z, G, A, B, $Q^1$, $Q^2$ and D
are each as defined in the description, to a plurality of processes for their preparation and to their use as pesticides and herbicides.

14 Claims, No Drawings

PHENYL SUBSTITUTED 4-HYDROXY TETRAHYDROXYPYRIDONE

The present invention relates to novel phenyl-substituted 4-hydroxy-tetrahydro-pyridones, to a plurality of processes for their preparation and to their use as pesticides and herbicides.

It is known that certain tetrahydropyridones have herbicidal properties: JP 0832530. Moreover, specific 4-hydroxytetrahydropyridones having acaricidal, insecticidal and herbicidal properties are known: JP 11152273.

However, the activity and activity spectrum of these compounds is, in particular at low application rates and concentrations, not always entirely satisfactory. Furthermore, the compatibility of these compounds with plants is not always sufficient.

This invention, accordingly, provides novel compounds of the formula (I)

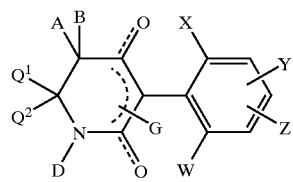
(I)

in which

W represents hydrogen, alkyl, alkenyl, alkinyl, halogen, halogenoalkyl or alkoxy, X represents halogen, alkyl, alkoxy, alkenyl, alkinyl, halogenoalkyl, halogenoalkoxy, cyano or in each case optionally substituted phenyl, phenoxy, phenylthio, phenylalkoxy or phenylalkylthio, Y represents hydrogen, alkyl, halogen, alkoxy, alkenyl, alkinyl or optionally substituted aryl or hetaryl, Z represents hydrogen, halogen, alkyl, alkoxy, halogenoalkyl, halogenoalkoxy or cyano, A represents hydrogen, in each case optionally halogen-substituted alkyl, alkenyl, alkoxyalkyl, optionally substituted cycloalkyl or cycloalkyl-alkyl in which optionally at least one ring atom is replaced by a heteroatom, or in each case optionally halogen-, alkyl-, halogenoalkyl-, alkoxy-, halogenoalkoxy-, cyano- or nitro-substituted aryl, arylalkyl, hetaryl or hetarylalkyl, B represents hydrogen or alkyl, or A and B together with the carbon atom to which they are attached represent a saturated or unsaturated, unsubstituted or substituted cycle which optionally contains at least one heteroatom, A and $Q^1$ together represent alkenediyl which is optionally substituted by in each case optionally substituted alkyl or alkoxy or, D represents hydrogen, D also represents an optionally substituted radical from the group consisting of alkenyl, alkinyl, alkoxyalkyl, optionally substituted cycloalkyl and cycloalkyl-alkyl in which optionally one or more ring members are replaced by heteroatoms, D and $Q^1$ together represent alkanediyl which is optionally substituted by in each case optionally substituted alkyl or alkoxy or $Q^1$ represents hydrogen, alkyl, alkoxyalkyl, optionally substituted cycloalkyl (in which optionally one methylene group is replaced by oxygen or sulphur) or optionally substituted phenyl, or $Q^2$ represents hydrogen or alkyl, $Q^1$ and $Q^2$ together with the carbon atom to which they are attached represent an unsubstituted or substituted cycle which optionally contains a heteroatom, G represents hydrogen (a) or represents one of the groups (b)

(c)
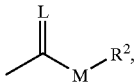

(d)
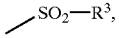

(e)
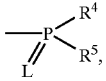

(f)
E   or (g)
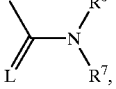

in which

E represents a metal ion or an ammonium ion,

L represents oxygen or sulphur,

M represents oxygen or sulphur, $R^1$ represents in each case optionally halogen-substituted alkyl, alkenyl, alkoxyalkyl, alkylthioalkyl, polyalkoxyalkyl or optionally halogen-, alkyl- or alkoxy-substituted cycloalkyl in which one or more methylene groups may be replaced by heteroatoms, in each case optionally substituted phenyl, phenylalkyl, hetaryl, phenoxyalkyl or hetaryloxyalkyl, $R^2$ represents in each case optionally halogen-substituted alkyl, alkenyl, alkoxyalkyl, polyalkoxyalkyl or represents or in each case optionally substituted cycloalkyl, phenyl or benzyl, $R^3$, $R^4$ and $R^5$ independently of one another represent in each case optionally halogen-substituted alkyl, alkoxy, alkylamino, dialkylamino, alkylthio, alkenylthio, cycloalkylthio and represent in each case optionally substituted phenyl, benzyl, phenoxy or phenylthio, and $R^6$ and $R^7$ independently of one another represent hydrogen, in each case optionally halogen-substituted alkyl, cycloalkyl, alkenyl, alkoxy, alkoxyalkyl, represent optionally substituted phenyl, represent optionally substituted benzyl, or together with the N atom to which they are attached represent a ring which is optionally interrupted by oxygen or sulphur.

Depending inter alia on the nature of the substituents, the compounds of the formula (I) can be present as geometrical and/or optical isomers or isomer mixtures in varying composition which, if appropriate, can be separated in a customary manner. The present invention provides both the pure isomers and the isomer mixtures, their preparation and use, and also compositions comprising them. However, hereinbelow, for the sake of simplicity, only compounds of the formula (I) are referred to, although this may mean both the pure compounds and, if appropriate, mixtures with varying contents of isomeric compounds.

Depending on the location of the substituent G, the compounds of the formula (I) can be present in the two isomeric forms of the formulae (I-A) and (I-B),

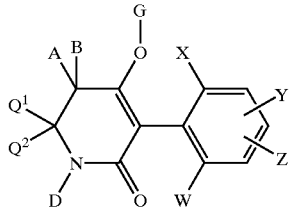
(I-A)

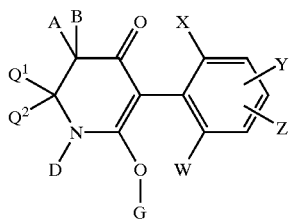
(I-B)

which is meant to be indicated by the broken line in formula (I).

The compounds of the formulae (I-A) and (I-B) can be present both as mixtures and in the form of their pure isomers. Mixtures of the compounds of the formulae (I-A) and (I-B) can, if appropriate, be separated in a manner known per se by physical methods, for example by chromatographic methods.

For reasons of clarity, hereinbelow only one of the possible isomers is shown in each case. This does not exclude the fact that the compounds are, if appropriate, present in the form of the isomer mixtures or in the respective other isomeric form.

Taking into account the different meanings (a), (b), (c), (d), (e), (f) and (g) of group G, the following principal structures (I-a) to (I-g) result (I-a):

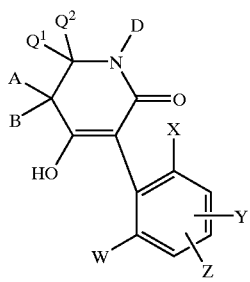

(I-b):

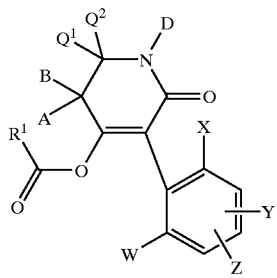

(I-c):

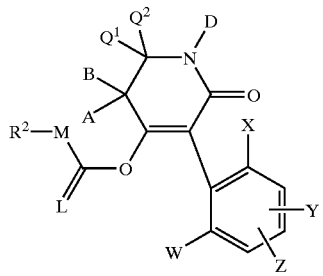

(I-d):

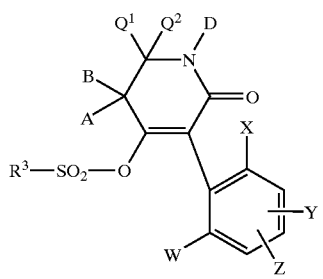

(I-e):

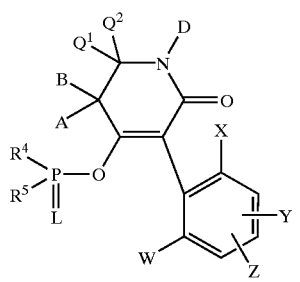

(I-f):

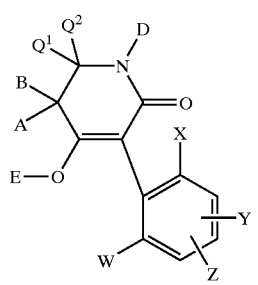

(I-g):

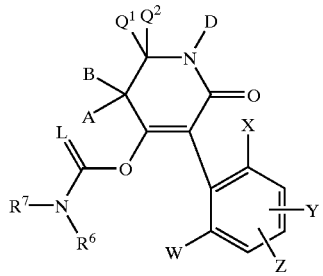

in which

A, B, D, E, L, M, $Q^1$, $Q^2$, W, X, Y, Z, $R^1$, $R^2$, $R^3$, $R^4$, $R^5$, $R^6$ and $R^7$ are each as defined above.

Furthermore, it has been found that the novel compounds of the formula (I) can be obtained by one of the processes described below:

(A) Substituted tetrahydropyridine-2,4-di ones of their enols of the formula (I-a)

(I-a)

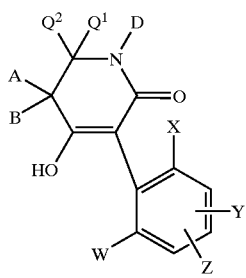

in which

A, B, D, $Q^1$, $Q^2$, W, X, Y and Z are each as defined above, are obtained when N-acylamino acid esters of the formula (II)

(II)

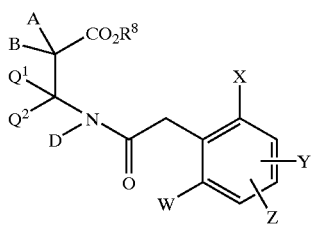

in which

A, B, D, $Q^1$, $Q^2$, W, X, Y and Z are each as defined above, and $R^8$ represents alkyl (preferably $C_1$–$C_6$-alkyl), are condensed intramolecularly in the presence of a diluent and in the presence of a base.

Furthermore, it has been found (B) that compounds of the formulae (I-a) to (I-g) shown above in which A, B, D, G, $Q^1$, $Q^2$, W, X, Y and Z are each as defined above are obtained when compounds of the formulae (I-a') to (I-g'), (I-a'):

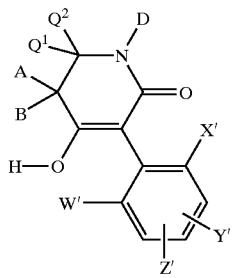

(I-b'):

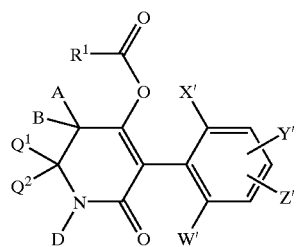

(I-c'):

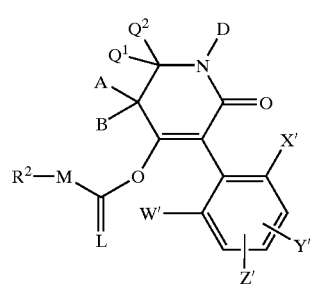

(I-d'):

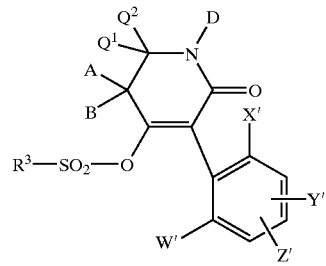

(I-e'):

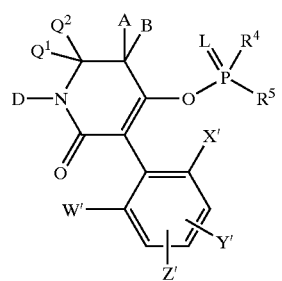

(I-f'):

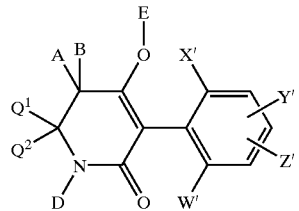

(I-9'):

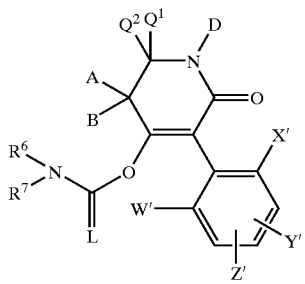

in which

A, B, D, $R^1$, $R^2$, $R^3$, $R^4$, $R^5$, $R^6$, $R^7$, E, L, M, $Q^1$, $Q^2$, W', X', Y' and Z' are each as defined above and where at least one of the radicals W', X', Y' represents chlorine, bromine or iodine, preferably bromine, and Z' does not represent bromine or iodine, α) are initially reacted with silylacetylene of the formula (III)

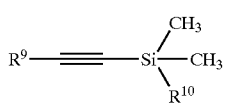

in which $R^9$ represents hydrogen and $R^{10}$ represents $C_1$–$C_4$-alkyl or phenyl, in particular methyl or tert-butyl, in the presence of a solvent, a base and a catalyst, particularly suitable catalysts being palladium complexes, and the silyl group is then removed, or β) are reacted with vinylstannanes of the formula (IV)

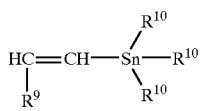

in which $R^9$ represents hydrogen, methyl or ethyl and $R^{10}$ represents $C_1$–$C_4$-alkyl, in particular butyl, in the presence of a solvent, if appropriate in the presence of a base and in the presence of a catalyst, particularly suitable catalysts being palladium complexes, or γ) in the specific case where Y' represents chlorine, bromine or iodine, preferably bromine, are reacted with boronic acids of the formula (V)

(V)

in which

Y represents optionally substituted phenyl or hetaryl in the presence of a solvent, a base and a catalyst, particularly suitable catalysts being palladium complexes.

Moreover, it has been found (C) that the compounds of the formula (I-b) shown above in which A, B, D, $Q^1$, $Q^2$, $R^1$, W, X, Y and Z are each as defined above are obtained when compounds of the formula (I-a) shown above in which A, B, D, $Q^1$, $Q^2$, W, X, Y and Z are each as defined above are in each case reacted (α) with acid halides of the formula (VI)

(VI)

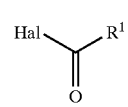

in which $R^1$ is as defined above and

Hal represents halogen (in particular chlorine or bromine) or (β) with carboxylic anhydrides of the formula (VII)

$R^1$—CO—O—CO—$R^1$ (VII)

in which $R^1$ is as defined above, if appropriate in the presence of a diluent and if appropriate in the presence of an acid binder;

(D) that the compounds of the formula (I-c) shown above in which A, B, D, $Q^1$, $Q^2$, $R^2$, M, W, X, Y and Z are each as defined above and L represents oxygen are obtained when compounds of the formula (I-a) shown above in which A, B, D, $Q^1$, $Q^2$, W, X, Y and Z are each as defined above are in each case reacted with chloroformic esters or chloroformic thioesters of the formula (VIII)

$R^2$—M—CO—Cl (VIII)

in which $R^2$ and M are each as defined above, if appropriate in the presence of a diluent and if appropriate in the presence of an acid binder;

(E) that compounds of the formula (I-c) shown above in which A, B, D, $Q^1$, $Q^2$, $R^2$, M, W, X, Y and Z are each as defined above and L represents sulphur are obtained when compounds of the formula (I-a) shown above in which A, B, D, $Q^1$, $Q^2$, W, X, Y and Z are each as defined above are in each case reacted with chloromonothioformic esters or chlorodithioformic esters of the formula (IX)

(IX)

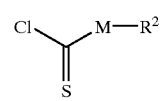

in which

M and $R^2$ are each as defined above, if appropriate in the presence of a diluent and if appropriate in the presence of an acid binder and (F) that compounds of the formula (I-d) shown above in which A, B, D, Q¹, Q², R³, W, X, Y and Z are each as defined above are obtained when compounds of the formula (I-a) shown above in which A, B, D, Q¹, Q², W, X, Y and Z are each as defined above are in each case reacted
with sulphonyl chlorides of the formula (X)

      (X)

in which
R³ is as defined above,
if appropriate in the presence of a diluent and if appropriate in the presence of an acid binder,
(G) that compounds of the formula (I-e) shown above in which A, B, D, L, Q¹, Q², R⁴, R⁵, W, X, Y and Z are each as defined above are obtained when compounds of the formula (I-a) shown above in which A, B, D, Q¹, Q², W, X, Y and Z are each as defined above are in each case reacted
with phosphorus compounds of the formula (XI)

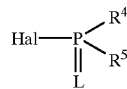      (XI)

in which
L, R⁴ and R⁵ are each as defined above and
Hal represents halogen (in particular chlorine or bromine),
if appropriate in the presence of a diluent and if appropriate in the presence of an acid binder,
(H) that compounds of the formula (I-f) shown above in which A, B, D, E, Q¹, Q², W, X, Y and Z are each as defined above are obtained when compounds of the formula (I-a) in which A, B, D, Q¹, Q², W, X, Y and Z are each as defined above are in each case reacted
with metal compounds or amines of the formulae (XII) and (XIII)

Me(OR¹¹)_t      (XII)

      (XIII)

in which
Me represents a mono- or divalent metal (preferably an alkali metal or alkaline earth metal such as lithium, sodium, potassium, magnesium or calcium),
t represents the number 1 or 2 and
R¹¹, R¹², R¹³ independently of one another each represent hydrogen or alkyl (preferably C₁–C₈-alkyl),
if appropriate in the presence of a diluent,
(I) that compounds of the formula (I-g) shown above in which A, B, D, L, Q¹, Q², R⁶, R⁷, W, X, Y and Z are each as defined above are obtained when compounds of the formula (I-a) shown above in which A, B, D, Q¹, Q², W, X, Y and Z are each as defined above are in each case
(α) reacted with isocyanates or isothiocyanates of the formula (XIV)

R⁶—N=C=L      (XIV)

in which
R⁶ and L are each as defined above,
if appropriate in the presence of a diluent and if appropriate in the presence of a catalyst or
(β) are reacted with carbamoyl chlorides or thiocarbamoyl chlorides of the formula (XV)

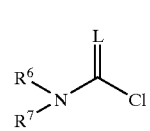      (XV)

in which
L, R⁶ and R⁷ are each as defined above,
if appropriate in the presence of a diluent and if appropriate in the presence of an acid binder.
Furthermore, it has been found that the novel compounds of the formula (I) have very good activity as pesticides, preferably as insecticides and akaricides, and also as herbicides.

The formula (I) provides a general definition of the compounds according to the invention. Preferred substituents or ranges of the radicals listed in the formulae mentioned above and below are illustrated below:

W preferably represents hydrogen, C₁–C₆-alkyl, C₂–C₄-alkenyl, ethinyl, fluorine, chlorine, bromine, C₁–C₄-halogenoalkyl or C₁–C₆-alkoxy.
X preferably represents fluorine, chlorine, bromine, C₁–C₆-alkyl, C₁–C₄-halogenoalkyl, C₁–C₆-alkoxy, C₂–C₄-alkenyl, ethinyl, C₁–C₄-halogenoalkoxy, cyano or in each case optionally halogen-, C₁–C₆-alkyl-, C₁–C₆-alkoxy-, C₁–C₄-halogenoalkyl-, C₁–C₄-halogenoalkoxy-, nitro- or cyano-substituted phenyl or benzyloxy.
Y preferably represents hydrogen, C₁–C₆-alkyl, fluorine, chlorine, bromine, C₁–C₆-alkoxy, C₂–C₄-alkenyl, ethinyl or represents one of the radicals

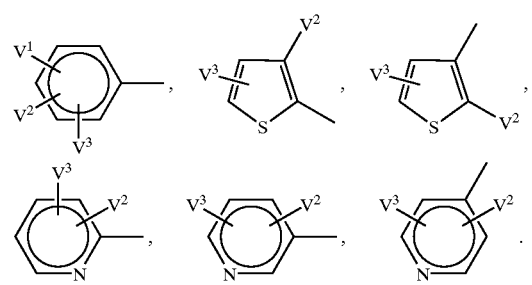

V¹ preferably represents hydrogen, halogen, C₁–C₁₂-alkyl, C₁–C₆-alkoxy, C₁–C₆-alkylthio, C₁–C₄-halogenoalkyl, C₁–C₄-halogenoalkoxy, nitro, cyano or represents phenyl, phenoxy, phenoxy-C₁–C₄-alkyl, phenyl-C₁–C₄-alkoxy, phenylthio-C₁–C₄-alkyl or phenyl-C₁–C₄-alkylthio, each of which is optionally mono- or polysubstituted by halogen, C₁–C₆-alkyl, C₁–C₆-alkoxy, C₁–C₄-halogenoalkyl, C₁–C₄-halogenoalkoxy, nitro or cyano.
V² preferably represents hydrogen, fluorine, chlorine C₁–C₆-alkyl, C₁–C₆-alkoxy, C₁–C₄-halogenoalkyl or C₁–C₄-halogenoalkoxy.
V³ preferably represents hydrogen, fluorine, chlorine, methyl or methoxy.
Z preferably represents hydrogen, fluorine, chlorine, bromine, C₁–C₆-alkyl, C₁–C₄-halogenoalkyl, C₁–C₆- alkoxy, $C_1$–$C_4$-halogenoalkoxy or cyano, with the proviso that W, X and Z do not represent bromine, $C_2$–$C_4$-alkenyl and ethinyl if Y represents $V^1$-, $V^2$- and $V^3$-substituted phenyl or hetaryl, and that at most two of the radicals W, X and Y may represent $C_2$–$C_4$-alkenyl and ethinyl, with the proviso that none of the other radicals W, X, Y and Z may represent bromine.

A preferably represents hydrogen or in each case optionally halogen-substituted $C_1$–$C_{12}$-alkyl, $C_3$–$C_8$-alkenyl, $C_1$–$C_6$-alkoxy-$C_1$–$C_4$-alkyl, optionally halogen-, $C_1$–$C_4$-alkyl- or $C_1$–$C_4$-alkoxy-substituted $C_3$–$C_8$-cycloalkyl or $C_3$–$C_6$-cycloalkyl-$C_1$–$C_4$-alkyl in which optionally one or two not directly adjacent ring members are replaced by oxygen and/or sulphur, or represents in each case optionally halogen-, $C_1$–$C_6$-alkyl-, $C_1$–$C_6$-halogenoalkyl-, $C_1$–$C_6$-alkoxy-, $C_1$–$C_6$-halogenoalkoxy-, cyano- or nitro-substituted phenyl, benzyl, hetaryl having 5 or 6 ring members (for example furanyl, pyridyl, imidazolyl, triazolyl, pyrazolyl, pyrimidyl, thiazolyl or thienyl) or hetaryl-$C_1$–$C_4$-alkyl having 5 or 6 ring members (for example pyridyl, pyrimidyl or thiazolyl).

B preferably represents hydrogen or $C_1$–$C_6$-alkyl.

A, B and the carbon atom to which they are attached preferably represent saturated $C_3$–$C_{10}$-cycloalkyl or unsaturated $C_5$–$C_{10}$-cycloalkyl in which optionally one ring member is replaced by oxygen or sulphur and which are optionally mono- or disubstituted by $C_1$–$C_6$-alkyl, $C_3$–$C_8$-cycloalkyl, $C_1$–$C_6$-halogeno-alkyl, $C_1$–$C_6$-alkoxy, $C_1$–$C_6$-alkylthio, halogen or phenyl, or A and $Q^1$ together preferably represent $C_3$–$C_6$-alkanediyl which is optionally mono- or disubstituted by identical or different substituents from the group consisting of $C_1$–$C_4$-alkyl and $C_1$–$C_4$-alkoxy.

D preferably represents hydrogen.

D also preferably represents in each case optionally halogen-substituted $C_3$–$C_8$-alkenyl, $C_3$–$C_8$-alkinyl, $C_1$–$C_6$-alkoxy-$C_2$–$C_6$-alkyl, optionally halogen-, $C_1$–$C_4$-alkyl-, $C_1$–$C_4$-alkoxy- or $C_1$–$C_4$-halogenoalkyl-substituted $C_3$–$C_8$-cycloalkyl or $C_3$–$C_6$-cycloalkyl-$C_1$–$C_4$-alkyl in which optionally one ring member is replaced by oxygen or sulphur.

D and $Q^1$ together preferably represent $C_3$–$C_6$-alkanediyl which is optionally mono- or disubstituted by identical or different substituents from the group consisting of $C_1$–$C_4$-alkyl and $C_1$–$C_4$-alkoxy, or $Q^1$ preferably represents hydrogen, $C_1$–$C_6$-alkyl, $C_1$–$C_6$-alkoxy-$C_1$–$C_2$-alkyl, optionally fluorine-, chlorine-, $C_1$–$C_4$-alkyl-, $C_1$–$C_2$-halogenoalkyl- or $C_1$–$C_4$-alkoxy-substituted $C_3$–$C_8$-cycloalkyl in which optionally one methylene group is replaced by oxygen or sulphur or optionally halogen-, $C_1$–$C_4$-alkyl-, $C_1$–$C_4$-alkoxy-, $C_1$–$C_2$-halogenoalkyl-, $C_1$–$C_2$-halogenoalkoxy-, cyano or nitro-substituted phenyl, or $Q^2$ preferably represents hydrogen or $C_1$–$C_4$-alkyl.

$Q^1$ and $Q^2$ together with the carbon atom to which they are attached preferably represent optionally $C_1$–$C_6$-alkyl-, $C_1$–$C_6$-alkoxy- or $C_1$–$C_2$-halogenoalkyl-substituted $C_3$–$C_7$-cycloalkyl in which optionally one ring member is replaced by oxygen or sulphur.

G preferably represents hydrogen (a) or represents one of the groups

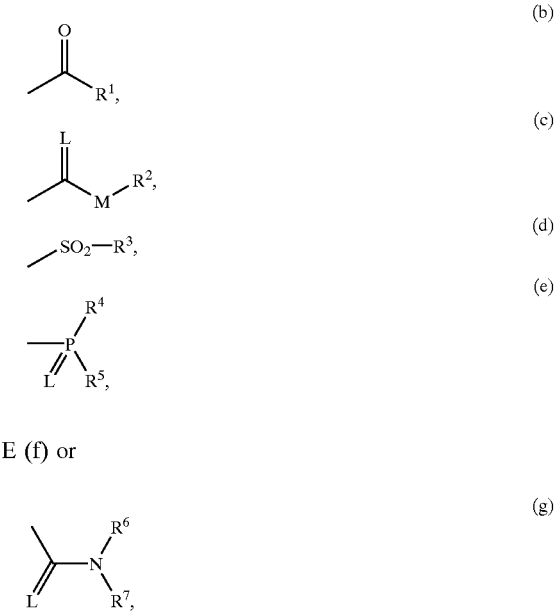

represents especially (a), (b), (c), (d) or (g),
in which
E represents a metal ion or an ammonium ion,
L represents oxygen or sulphur and
M represents oxygen or sulphur, $R^1$ preferably represents in each case optionally halogen-substituted $C_1$–$C_{20}$-alkyl, $C_2$–$C_{20}$-alkenyl, $C_1$–$C_8$-alkoxy-$C_1$–$C_8$-alkyl, $C_1$–$C_8$-alkylthio-$C_1$–$C_8$-alkyl, poly-$C_1$–$C_8$-alkoxy-$C_1$–$C_8$-alkyl or optionally halogen-, $C_1$–$C_6$-alkyl- or $C_1$–$C_6$-alkoxy-substituted $C_3$–$C_8$-cycloalkyl in which optionally one or more (preferably one or two) not directly adjacent ring members are replaced by oxygen and/or sulphur, represents optionally halogen-, cyano-, nitro-, $C_1$–$C_6$-alkyl-, $C_1$–$C_6$-alkoxy-, $C_1$–$C_6$-halogenoalkyl-, $C_1$–$C_6$-halogenoalkoxy-, $C_1$–$C_6$-alkylthio- or $C_1$–$C_6$-alkylsulphonyl-substituted phenyl, represents optionally halogen-, nitro-, cyano-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl-$C_1$–$C_6$-alkyl, represents optionally halogen-, $C_1$–$C_6$-alkyl or trifluoromethyl-substituted 5- or 6-membered hetaryl (for example pyrazolyl, thiazolyl, pyridyl, pyrimidyl, furanyl or thienyl), represents optionally halogen- or $C_1$–$C_6$-alkyl-substituted phenoxy-$C_1$–$C_6$-alkyl or represents optionally halogen-, amino- or $C_1$–$C_6$-alkyl-substituted 5- or 6-membered hetaryloxy-$C_1$–$C_6$-alkyl (for example pyridyloxy-$C_1$–$C_6$-alkyl, pyrimidyloxy-$C_1$–$C_6$-alkyl or thiazolyloxy-$C_1$–$C_6$-alkyl).

$R^2$ preferably represents in each case optionally halogen-substituted $C_1$–$C_{20}$-alkyl, $C_2$–$C_{20}$-alkenyl, $C_1$–$C_8$-alkoxy-$C_2$–$C_8$-alkyl, poly-$C_1$–$C_8$-alkoxy-$C_2$–$C_8$-alkyl, represents optionally halogen-, $C_1$–$C_6$-alkyl- or $C_1$–$C_6$-alkoxy-substituted $C_3$–$C_8$-cycloalkyl or represents in each case optionally halogen-, cyano-, nitro-, $C_1$–$C_6$-alkyl-, $C_1$–$C_6$-alkoxy-, $C_1$–$C_6$-halogenoalkyl- or $C_1$–$C_6$-halogenoalkoxy-substituted phenyl or benzyl.

$R^3$ preferably represents optionally halogen-substituted $C_1$–$C_8$-alkyl or represents in each case optionally halogen-, $C_1$–$C_6$-alkyl-, $C_1$–$C_6$-alkoxy-, $C_1$–$C_4$-halogenoalkyl-, $C_1$–$C_4$-halogenoalkoxy-, cyano- or nitro-substituted phenyl or benzyl, $R^4$ and $R^5$ independently of one another preferably represent in each case optionally halogen-substituted $C_1$–$C_8$-alkyl, $C_1$–$C_8$-alkoxy, $C_1$–$C_8$-alkylamino, di-($C_1$–$C_8$-alkyl)amino, $C_1$–$C_8$-alkylthio, $C_2$–$C_8$-alkenylthio, $C_3$–$C_7$-cycloalkylthio or represent in each case optionally halogen-, nitro-, cyano-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkyl- or $C_1$–$C_4$-halogenoalkyl-substituted phenyl, benzyl, phenoxy or phenylthio, $R^6$ and $R^7$ independently of one another preferably represent hydrogen, represent in each case optionally halogen-substituted $C_1$–$C_8$-alkyl, $C_3$–$C_8$-cycloalkyl, $C_1$–$C_8$-alkoxy, $C_3$–$C_8$-alkenyl, $C_1$–$C_8$-alkoxy-$C_1$–$C_8$-alkyl, represent optionally halogen-, $C_1$–$C_8$-halogenoalkyl-, $C_1$–$C_8$-alkyl- or $C_1$–$C_8$-alkoxy-substituted phenyl, optionally halogen-, $C_1$–$C_8$-alkyl-, $C_1$–$C_8$-halogenoalkyl- or $C_1$–$C_8$-alkoxy-substituted benzyl or together represent an optionally $C_1$–$C_4$-alkyl-substituted $C_3$–$C_6$-alkylene radical in which optionally one carbon atom is replaced by oxygen or sulphur.

In the radical definitions mentioned as being preferred, halogen, also as substituent, such as, for example, in halogenoalkyl, represents fluorine, chlorine, bromine and iodine, in particular fluorine and chlorine.

W particularly preferably represents hydrogen, $C_1$–$C_4$-alkyl, $C_2$–$C_3$-alkenyl, ethinyl, fluorine, chlorine, bromine, trifluoromethyl or $C_1$–$C_4$-alkoxy, X particularly preferably represents fluorine, chlorine, bromine, $C_1$–$C_4$-alkyl, $C_1$–$C_4$-alkoxy, $C_2$–$C_3$-alkenyl, ethinyl, $C_1$–$C_2$-halogenoalkyl, $C_1$–$C_2$-halo-genoalkoxy or cyano, Y particularly preferably represents hydrogen, $C_1$–$C_4$-alkyl, fluorine, chlorine, bromine, $C_1$–$C_4$-alkoxy, $C_2$–$C_3$-alkenyl, ethinyl, 2-thienyl, 3-thienyl or represents the radical

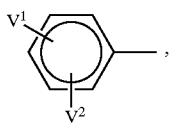

$V^1$ particularly preferably represents hydrogen, fluorine, chlorine, bromine, $C_1$–$C_6$-alkyl, $C_1$–$C_4$-alkoxy, $C_1$–$C_4$-alkylthio, $C_1$–$C_2$-halogenoalkyl, $C_1$–$C_2$-halogenoalkoxy, nitro, cyano or phenyl, $V^2$ particularly preferably represents hydrogen, fluorine, chlorine $C_1$–$C_4$-alkyl, $C_1$–$C_4$-alkoxy, $C_1$–$C_2$-halogenoalkyl or $C_1$–$C_2$-halogenoalkoxy.

Z particularly preferably represents hydrogen, fluorine, chlorine, bromine, $C_1$–$C_4$-alkyl, $C_1$–$C_2$-halogenoalkyl, $C_1$–$C_4$-alkoxy or $C_1$–$C_2$-halogenoalkoxy, with the proviso that W, X and Z do not represent bromine, $C_2$–$C_3$-alkenyl and ethinyl if Y represents $V^1$- and $V^2$-substituted phenyl, 2-thienyl or 3-thienyl, and that only one of the radicals W, X and Y may represent $C_2$–$C_3$-alkenyl and ethinyl, with the proviso that none of the other radicals W, X, Y and Z may represent bromine.

A particularly preferably represents hydrogen, in each case optionally fluorine-substituted $C_1$–$C_8$-alkyl, $C_1$–$C_4$-alkoxy-$C_1$–$C_2$-alkyl, optionally fluorine-, chlorine-, methyl, ethyl- or methoxy-substituted $C_5$–$C_6$-cycloalkyl or $C_3$–$C_6$-cycloalkyl-$C_1$–$C_2$-alkyl, in which optionally one ring member is replaced by oxygen or sulphur or in each case optionally fluorine-, chlorine-, bromine-, $C_1$–$C_4$-alkyl-, $C_1$–$C_2$-halogenoalkyl-, $C_1$–$C_4$-alkoxy- or $C_1$–$C_2$-halogenoalkoxy-substituted phenyl or benzyl.

B particularly preferably represents hydrogen or $C_1$–$C_4$-alkyl.

A, B and the carbon atom to which they are attached particularly preferably represent saturated $C_5$–$C_7$-cycloalkyl in which optionally one ring member is replaced by oxygen and which is optionally monosubstituted by $C_1$–$C_4$-alkyl, trifluoromethyl or $C_1$–$C_4$-alkoxy, or A and $Q^1$ together particularly preferably represent $C_3$–$C_4$-alkanediyl, D particularly preferably represents hydrogen, D particularly preferably also represents in each case optionally fluorine-substituted $C_3$–$C_6$-alkenyl, $C_1$–$C_4$-alkoxy-$C_2$–$C_6$-alkyl, represents $C_3$–$C_7$-cycloalkyl or $C_3$–$C_6$-cycloalkyl-$C_1$–$C_2$-alkyl in which optionally one methylene group is replaced by oxygen.

D and $Q^1$ together particularly preferably represent $C_3$–$C_4$-alkanediyl.

$Q^1$ particularly preferably represents hydrogen, $C_1$–$C_4$-alkyl, $C_1$–$C_4$-alkoxy-$C_1$–$C_2$-alkyl or optionally methyl- or methoxy-substituted $C_3$–$C_6$-cycloalkyl in which optionally one methylene group is replaced by oxgen.

$Q^2$ particularly preferably represents hydrogen, methyl or ethyl.

$Q^1$ and $Q^2$ together with the carbon to which they are attached particularly preferably represent optionally $C_1$–$C_4$-alkyl- or $C_1$–$C_4$-alkoxy-substituted saturated $C_5$–$C_6$-cycloalkyl in which optionally one ring member is replaced by oxygen.

G particularly preferably represents hydrogen (a) or represents one of the groups (b)

(c)

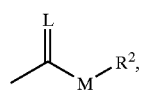

(d)

(e)

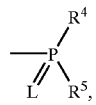

E (f) or (g)

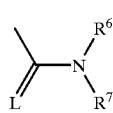

represents especially (a), (b), (c), (d) or (g),
in which
E represents a metal ion or an ammonium ion,
L represents oxygen or sulphur and
M represents oxygen or sulphur.

R¹ particularly preferably represents in each case optionally fluorine- or chlorine-substituted $C_1$–$C_{16}$-alkyl, $C_2$–$C_{16}$-alkenyl, $C_1$–$C_4$-alkoxy-$C_1$–$C_2$-alkyl, $C_1$–$C_4$-alkylthio-$C_1$–$C_2$-alkyl, or optionally fluorine-, chlorine-, $C_1$–$C_5$-alkyl- or $C_1$–$C_5$-alkoxy-substituted $C_3$–$C_7$-cycloalkyl in which optionally one or two not directly adjacent ring members are replaced by oxygen and/or sulphur, represents optionally fluorine-, chlorine-, bromine-, cyano-, nitro-, $C_1$–$C_4$-alkyl-, $C_1$–$C_4$-alkoxy-, trifluoromethyl- or trifluoromethoxy-substituted phenyl, represents in each case optionally fluorine-, chlorine-, bromine-, methyl-, ethyl- or trifluoromethyl-substituted pyridyl or thienyl, R² particularly preferably represents in each case optionally fluorine-substituted $C_1$–$C_{16}$-alkyl, $C_2$–$C_{16}$-alkenyl or $C_1$–$C_4$-alkoxy-$C_2$–$C_4$-alkyl, represents optionally methyl-, ethyl- or methoxy-substituted $C_3$–$C_7$-cycloalkyl or represents in each case optionally fluorine-, chlorine-, bromine-, cyano-, nitro-, $C_1$–$C_4$-alkyl-, $C_1$–$C_3$-alkoxy-, trifluoromethyl- or trifluoromethoxy-substituted phenyl or benzyl.

R³ particularly preferably represents optionally fluorine-substituted $C_1$–$C_6$-alkyl or represents in each case optionally fluorine-, chlorine-, bromine-, $C_1$–$C_4$-alkyl-, $C_1$–$C_4$-alkoxy-, trifluoromethyl-, trifluoromethoxy-, cyano- or nitro-substituted phenyl.

R⁴ particularly preferably represents $C_1$–$C_6$-alkyl, $C_1$–$C_6$-alkoxy, $C_1$–$C_6$-alkylamino, di-($C_1$–$C_6$-alkyl)amino, $C_1$–$C_6$-alkylthio, or represents in each case optionally fluorine-, chlorine-, bromine-, nitro-, cyano-, $C_1$–$C_3$-alkoxy-, trifluoromethoxy-, $C_1$–$C_3$-alkyl- or trifluoromethyl-substituted phenyl, benzyl, phenoxy or phenylthio.

R⁵ particularly preferably represents $C_1$–$C_4$-alkyl, $C_1$–$C_4$-alkoxy or $C_1$–$C_4$-alkylthio.

R⁶ particularly preferably represents hydrogen, $C_1$–$C_6$-alkyl, $C_3$–$C_6$-cycloalkyl, $C_1$–$C_6$-alkoxy, $C_3$–$C_6$-alkenyl, $C_1$–$C_6$-alkoxy-$C_1$–$C_6$-alkyl, represents optionally fluorine-, chlorine-, bromine-, trifluoromethyl-, $C_1$–$C_4$-alkyl- or $C_1$–$C_4$-alkoxy-substituted phenyl, represents optionally fluorine-, chlorine-, bromine-, methyl-, ethyl-, trifluoromethyl- or methoxy-substituted benzyl.

R⁷ particularly preferably represents hydrogen, $C_1$–$C_6$-alkyl or $C_3$–$C_6$-alkenyl.

R⁶ and R⁷ together particularly preferably represent an optionally methyl- or ethyl-substituted $C_4$–$C_5$-alkylene radical in which optionally one methylene group is replaced by oxygen or sulphur.

In the radical definitions mentioned as being particularly preferred, halogen, also as substituent, such as, for example, in halogenoalkyl, represents fluorine, chlorine, bromine and iodine, in particular fluorine and chlorine, particularly preferably fluorine.

W very particularly preferably represents hydrogen, fluorine, chlorine, bromine, methyl, ethyl, propyl or methoxy.

X very particularly preferably represents fluorine, chlorine, bromine, methyl, ethyl, n-propyl, iso-propyl, methoxy, ethoxy, n-propoxy, trifluoromethyl, difluoromethoxy, trifluoromethoxy or cyano (especially chlorine, bromine, methyl, ethyl, n-propyl or trifluoromethyl).

Y very particularly preferably represents hydrogen, methyl, ethyl, propyl, iso-propyl, fluorine, chlorine, bromine, methoxy, 2-thienyl, 3-thienyl or represents the radical

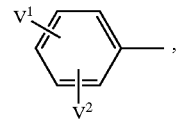

V¹ very particularly preferably represents hydrogen, fluorine, chlorine, bromine, methyl, ethyl, n-propyl, iso-propyl, n-butyl, iso-butyl, tert-butyl, methoxy, ethoxy, n-propoxy, iso-propoxy, trifluoromethyl or trifluoromethoxy, cyano or phenyl.

V² very particularly preferably represents hydrogen, fluorine, chlorine methyl, methoxy or trifluoromethyl.

Z very particularly preferably represents hydrogen, fluorine, chlorine, bromine, methyl, ethyl, methoxy or trifluoromethyl (especially hydrogen, fluorine, chlorine, bromine or methyl), with the proviso that W, X and Z do not represent bromine if Y represents V¹- and V²-substituted phenyl, 2-thienyl or 3-thienyl.

A very particularly preferably represents hydrogen, methyl, ethyl, propyl, isopropyl, butyl, iso-butyl, methoxymethyl, ethoxymethyl.

B very particularly preferably represents hydrogen, methyl or ethyl.

A, B and the carbon atom to which they are attached very particularly preferably represent saturated $C_5$–$C_6$-cycloalkyl in which optionally one ring member is replaced by oxygen and which is optionally monosubstituted by methyl, ethyl, n-propyl, isopropyl, butyl, trifluoromethyl, methoxy, ethoxy, n-propoxy or n-butoxy, or A and Q¹ together very particularly preferably represent $C_3$–$C_4$-alkanediyl, D very particularly preferably represents hydrogen, D very particularly preferably also represents allyl, 2-butenyl, methoxyethyl, ethoxyethyl, cyclopropyl, cyclopentyl or cyclohexyl.

D and Q¹ together very particularly preferably represent $C_3$–$C_4$-alkanediyl.

Q¹ very particularly preferably represents hydrogen, methyl, ethyl, propyl, isopropyl, cyclopropyl, cyclopentyl or cyclohexyl.

Q² very particularly preferably represents hydrogen, methyl or ethyl.

Q¹ and Q² together with the carbon to which they are attached very particularly preferably represent optionally methyl-, ethyl-, propyl-, iso-propyl-, methoxy-, ethoxy-, propoxy- or butoxy-substituted saturated $C_5$–$C_6$-cycloalkyl in which optionally one ring member is replaced by oxygen.

G very particularly preferably represents hydrogen (a) or represents one of the groups (b)

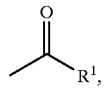

(c)

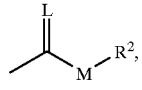

(d)

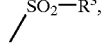

 (e)

E (f) or

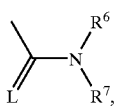 (g)

represents especially (a), (b), (c), (d) or (g),
in which
E represents a metal ion or an ammonium ion,
L represents oxygen or sulphur and
M represents oxygen or sulphur,
$R^1$ very particularly preferably represents in each case optionally fluorine- or chlorine-substituted $C_1$–$C_{14}$-alkyl, $C_2$–$C_{14}$-alkenyl, $C_1$–$C_4$-alkoxy-$C_1$–$C_2$-alkyl, $C_1$–$C_4$-alkylthio-$C_1$–$C_2$-alkyl or optionally fluorine-, chlorine-, methyl-, ethyl- or methoxy-substituted $C_3$–$C_6$-cycloalkyl in which optionally one or two not directly adjacent ring members are replaced by oxygen and/or sulphur,
represents optionally fluorine-, chlorine-, bromine-, cyano-, nitro-, methyl-, ethyl-, iso-propyl-, tert-butyl-, methoxy-, trifluoromethyl- or trifluoromethoxy-substituted phenyl,
represents in each case optionally fluorine-, chlorine-, bromine- or methyl-substituted thienyl or pyridyl,
$R^2$ very particularly preferably represents in each case optionally fluorine-substituted $C_1$–$C_{14}$-alkyl, $C_2$–$C_{14}$-alkenyl or $C_1$–$C_4$-alkoxy-$C_2$–$C_3$-alkyl,
represents optionally methyl-, ethyl- or methoxy-substituted $C_3$–$C_6$-cycloalkyl,
or represents in each case optionally fluorine-, chlorine-, cyano-, nitro-, methyl-, ethyl-, iso-propyl-, tert-butyl-, methoxy-, trifluoromethyl- or trifluoromethoxy-substituted phenyl or benzyl.
$R^3$ very particularly preferably represents optionally fluorine-substituted methyl, ethyl, n-propyl, iso-propyl or in each case optionally fluorine-, chlorine-, bromine-, methyl-, tert-butyl-, methoxy-, trifluoromethyl-, trifluoromethoxy-, cyano- or nitro-substituted phenyl.
$R^4$ very particularly preferably represents $C_1$–$C_4$-alkyl, $C_1$–$C_4$-alkoxy, $C_1$–$C_4$-alkylamino, di-($C_1$–$C_4$-alkyl)amino, $C_1$–$C_4$-alkylthio or represents in each case optionally fluorine-, chlorine-, bromine-, nitro-, cyano-, $C_1$–$C_2$-alkoxy-, trifluoromethoxy- or $C_1$–$C_3$-alkyl-substituted phenyl, phenoxy or phenylthio.
$R^5$ very particularly preferably represents methyl, ethyl, methoxy, ethoxy, methylthio or ethylthio.
$R^6$ very particularly preferably represents hydrogen, represents $C_1$–$C_4$-alkyl, $C_3$–$C_6$-cycloalkyl, $C_1$–$C_4$-alkoxy, $C_3$–$C_4$-alkenyl, $C_1$–$C_4$-alkoxy-$C_1$–$C_4$-alkyl.
$R^7$ very particularly preferably represents hydrogen, represents $C_1$–$C_4$-alkyl or $C_3$–$C_4$-alkenyl.
$R^6$ and $R^7$ together very particularly preferably represent a $C_5$–$C_6$-alkylene radical in which optionally one methylene group is replaced by oxygen or sulphur.
In the compounds of the formula (I) mentioned as being most preferred, the radicals are as defined below:

W most preferably represents hydrogen, fluorine, chlorine, bromine, methyl or ethyl,
X most preferably represents chlorine, bromine, methyl, ethyl, propyl or trifluoromethyl,
Y most preferably represents hydrogen, chlorine, bromine, fluorine, methyl, ethyl or the radical

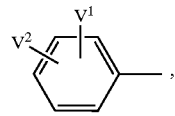

$V^1$ most preferably represents hydrogen, fluorine, chlorine, bromine, methyl, tert-butyl, methoxy, trifluoromethyl or phenyl,
$V^2$ most preferably represents hydrogen, fluorine, chlorine methyl, methoxy or trifluoromethyl,
Z most preferably represents hydrogen, bromine, chlorine or methyl,
A most preferably represents methyl, ethyl or propyl,
B most preferably represents methyl or ethyl,
A, B and the carbon atom to which they are attached most preferably represent saturated $C_5$–$C_6$-cycloalkyl in which optionally one ring member is replaced by oxygen and which is optionally monosubstituted by methyl, ethyl, methoxy, ethoxy, n-propoxy or n-butoxy.
D most preferably represents hydrogen,
D most preferably also represents cyclopropyl, cyclopentyl or cyclohexyl,
$Q^1$ and $Q^2$ most preferably represent hydrogen,
D and $Q^1$ together most preferably represent butanediyl,
G most preferably represents hydrogen (a) or represents one of the groups

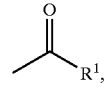 (b)

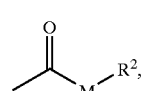 (c)

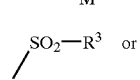 (d)

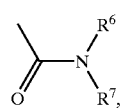 (g)

in which
M represents oxygen or sulphur,
$R^1$ most preferably represents $C_1$–$C_8$-alkyl, $C_2$–$C_4$-alkenyl, methoxymethyl, ethoxymethyl, ethylthiomethyl or optionally fluorine-, chlorine-, methyl-, ethyl- or methoxy-substituted cyclopropyl, cyclopentyl or cyclohexyl,
represents optionally fluorine-, chlorine-, bromine-, cyano-, nitro-, methyl-, ethyl-, iso-propyl-, tert-butyl-, methoxy-, trifluoromethyl- or trifluoromethoxy-substituted phenyl,
represents in each case optionally chlorine- or methyl-substituted thienyl or pyridyl,
$R^2$ most preferably represents in each case optionally fluorine-substituted $C_1$–$C_8$-alkyl, $C_2$–$C_4$-alkenyl or methoxyethyl, ethoxyethyl, propoxyethyl, iso-propoxyethyl, cyclopentyl or cyclohexyl, or represents in each case optionally fluorine-, chlorine-, cyano-, nitro-, methyl-, ethyl-, iso-propyl-, tert-butyl-, methoxy-, trifluoromethyl- or trifluoromethoxy-substituted phenyl or benzyl.

$R^3$ most preferably represents methyl, $R^6$ and $R^7$ together most preferably represent a $C_6$-alkylene radical in which optionally one methylene group is replaced by oxygen, or else W most preferably represents hydrogen, fluorine, chlorine, bromine, methyl or ethyl, X most preferably represents chlorine, bromine, methyl, ethyl, propyl or trifluoromethyl, Y most preferably represents hydrogen, methyl, ethyl, fluorine, chlorine, bromine or represents the radical

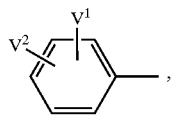

$V^1$ most preferably represents hydrogen, fluorine, chlorine, bromine, methyl, tert-butyl, methoxy, trifluoromethyl or phenyl, $V^2$ most preferably represents hydrogen, fluorine, chlorine methyl, methoxy or trifluoromethyl, Z most preferably represents hydrogen, chlorine, bromine or methyl, A and B most preferably represent hydrogen, D most preferably represents hydrogen, methyl, ethyl, propyl, iso-propyl, cyclopropyl, cyclopentyl or cyclohexyl, D and $Q^1$ together most preferably represent butanediyl, $Q^1$ most preferably represents methyl, ethyl or propyl, $Q^2$ most preferably represents methyl; if D and $Q^1$ together represent butanediyl, $Q^2$ may also represent hydrogen, $Q^1$ and $Q^2$ together with the carbon to which they are attached most preferably represent optionally methyl-, ethyl-, methoxy-, ethoxy-, propoxy- or butoxy-substituted $C_5$–$C_6$-cycloalkyl in which optionally one ring member is replaced by oxygen, G most preferably represents hydrogen (a) or represents one of the groups (b)

(c)

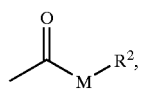

(d)

/SO$_2$—R$^3$ or (g)

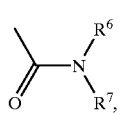

in which

M represents oxygen or sulphur, $R^1$ most preferably represents $C_1$–$C_8$-alkyl, $C_2$–$C_4$-alkenyl, methoxymethyl, ethoxymethyl, ethylthiomethyl or optionally fluorine-, chlorine-, methyl-, ethyl- or methoxy-substituted cyclopropyl, cyclopentyl or cyclohexyl, represents optionally fluorine-, chlorine-, bromine-, cyano-, nitro-, methyl-, ethyl-, iso-propyl-, tert-butyl-, methoxy-, trifluoromethyl- or trifluoromethoxy-substituted phenyl, represents in each case optionally chlorine- or methyl-substituted thienyl or pyridyl, $R^2$ most preferably represents in each case optionally fluorine-substituted $C_1$–$C_8$-alkyl, $C_2$–$C_4$-alkenyl or methoxyethyl, ethoxyethyl, propoxyethyl, iso-propoxyethyl, cyclopentyl or cyclohexyl, or represents in each case optionally fluorine-, chlorine-, cyano-, nitro-, methyl-, ethyl-, iso-propyl-, tert-butyl-, methoxy-, trifluoromethyl- or trifluoromethoxy-substituted phenyl or benzyl, $R^3$ most preferably represents methyl.

$R^6$ and $R^7$ together most preferably represent a $C_6$-alkylene radical in which optionally one methylene group is replaced by oxygen.

The above-mentioned general or preferred radical definitions or illustrations can be combined with one another as desired, i.e. including combinations between the respective ranges and preferred ranges. They apply both to the end products and, correspondingly, to precursors and intermediates.

Preference according to the invention is given to compounds of the formula (I) which contain a combination of the meanings listed above as being preferred (preferable).

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Most preference is given to compounds of the formula (I) in which G represents hydrogen.

Most preference is given to compounds of the formula (I) in which D represents hydrogen.

Furthermore, most preference is given to compounds of the formula (I) in which D represents optionally substituted alkenyl, alkinyl, alkoxyalkyl or cycloalkyl.

Saturated or unsaturated hydrocarbon radicals, such as alkyl or alkenyl, can in each case be straight-chain or branched as far as this is possible, also in combination with heteroatoms, such as, for example in alkoxy.

Unless indicated otherwise, optionally substituted radicals can be mono- or polysubstituted, where in the case of polysubstitution, the substituents can be identical or different.

Using according to process (A) ethyl N-[(2,3,4,6-tetramethyl)-phenylacetyl]-1-aminomethyl-cyclohexane-carboxylate as starting material, the course of the process according to the invention can be represented by the following reaction scheme:

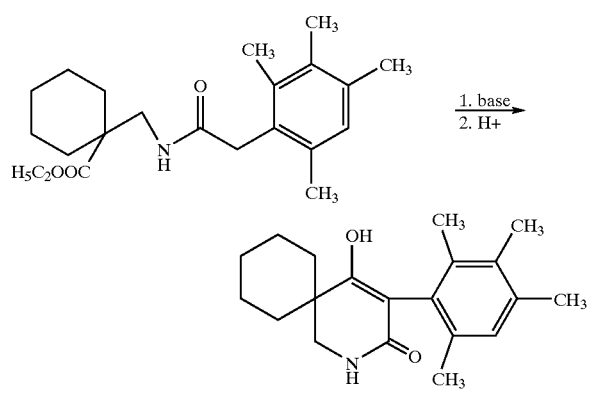

Using according to process (Bγ) 3-[(2-chloro-4-bromo-6-methyl)-phenyl]-6,6-dimethyl-piperidine-2,4-dione and 4-chlorophenylboronic acid as starting materials, the course of the reaction can be represented by the following scheme:

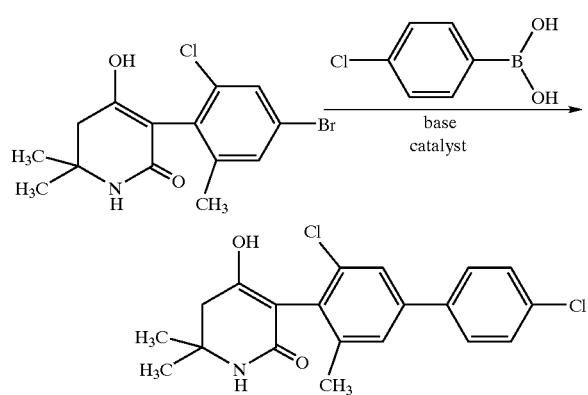

Using according to process (Cα) 3-[(2,4-dichloro-6-methyl)-phenyl]-6,6-dimethyl-piperidine-2,4-dione and pivaloyl chloride as starting materials, the course of the process according to the invention can be represented by the following reaction scheme:

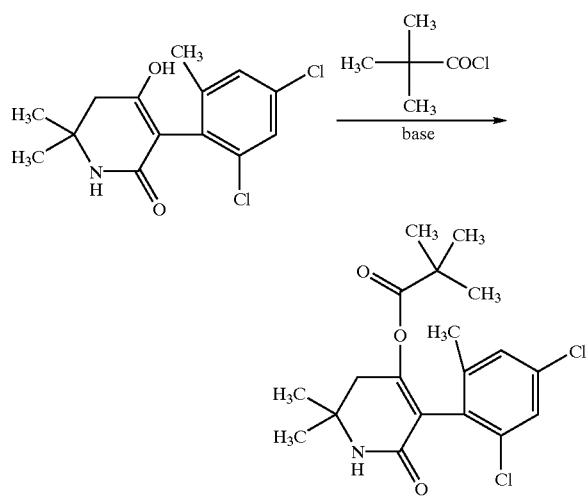

Using according to process (Cβ) 3-[(4-bromo-2-chloro-6-ethyl)-phenyl]-6,6-dimethyl-piperidine-2,4-dione and acetic anhydride as starting materials, the course of the process according to the invention can be represented by the following reaction scheme:

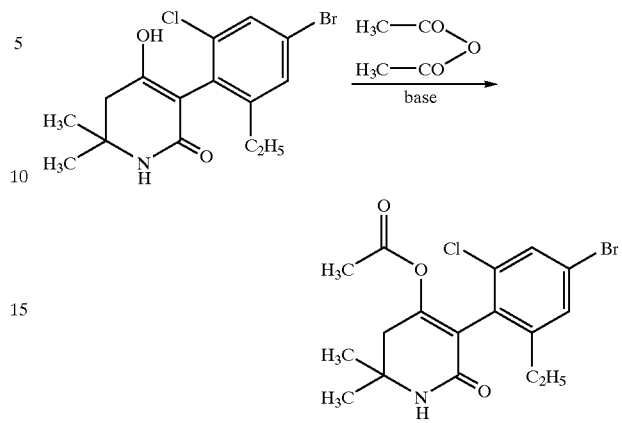

Using according to process (D) 3-[(2-chloro-6-ethyl-4-phenyl)-phenyl]-5,5-dimethylpiperidine-2,4-dione and ethoxyethyl chloroformate as starting materials, the course of the process according to the invention can be represented by the following reaction scheme:

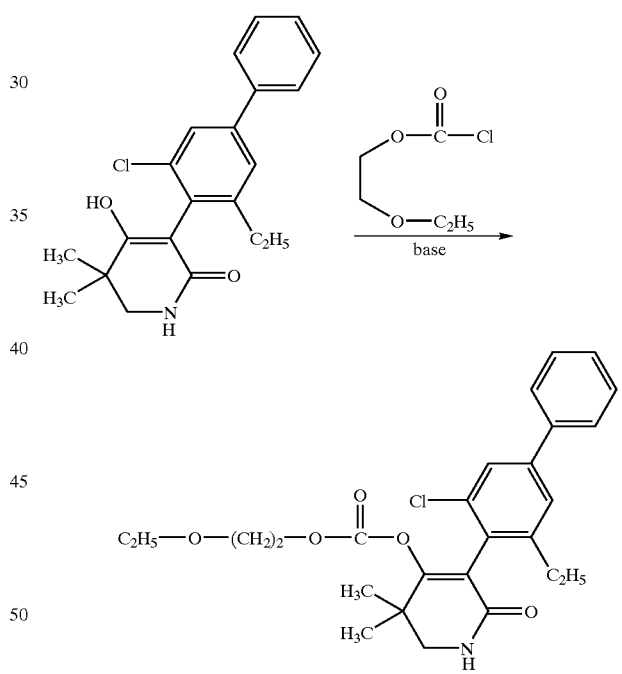

Using according to process (E) 3-[2,4,6-trichlorophenyl]-6,6-dimethyl-piperidine-2,4-dione and methyl chloromonothioformate as starting materials, the course of the reaction can be represented as follows:

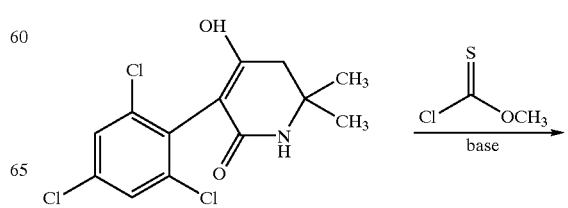

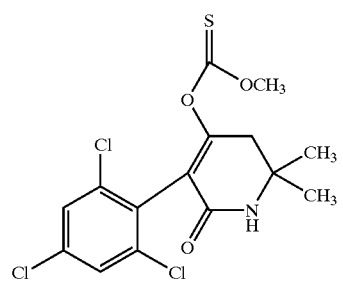

Using according to process (F) 3-(2,4-dichloro-6-methyl-phenyl)-6,6-dimethyl-piperidine-2,4-dione and methanesulphonyl chloride as starting materials, the course of the reaction can be represented by the following reaction scheme:

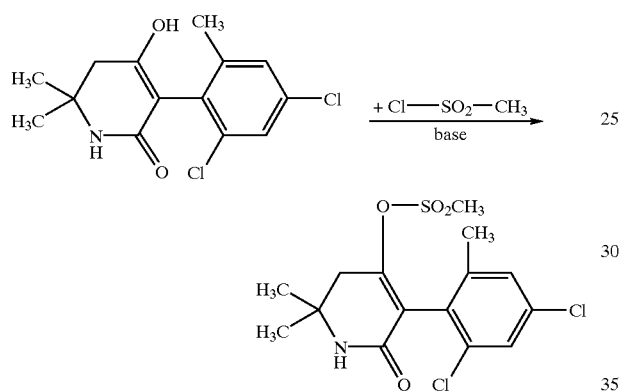

Using according to process (G) 2-(2-methyl-5-bromo-phenyl)-6,6-dimethyl-pyridine-2,4-dione and 2,2,2-trifluoroethyl methanethiophosphonyl chloride as starting materials, the course of the reaction can be represented by the following reaction scheme:

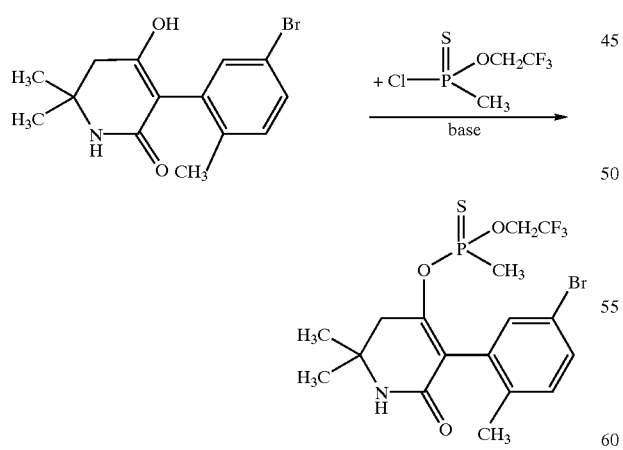

Using according to process (H) 3-(2,4-dichloro-phenyl)-6,6-dimethyl-piperidine-2,4-dione and NaOH as components, the course of the process according to the invention can be represented by the following reaction scheme:

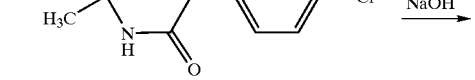
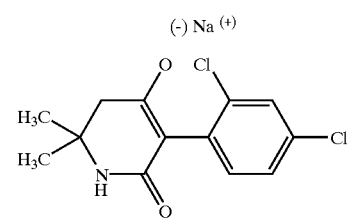

Using according to process (Iα) 3-(2,4-dichloro-6-methyl-phenyl)-6,6-dimethyl-piperidine-2,4-dione and ethyl isocyanate as starting materials, the course of the reaction can be represented by the following reaction scheme:

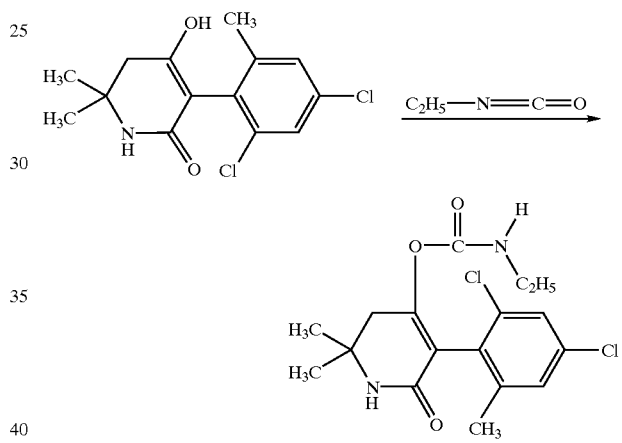

Using according to process (Iβ) 3-(2-chloro-4-bromo-phenyl)-6,6-dimethyl-piperidine-2,4-dione and dimethylcarbamoyl chloride as starting materials, the course of the reaction can be represented by the following scheme:

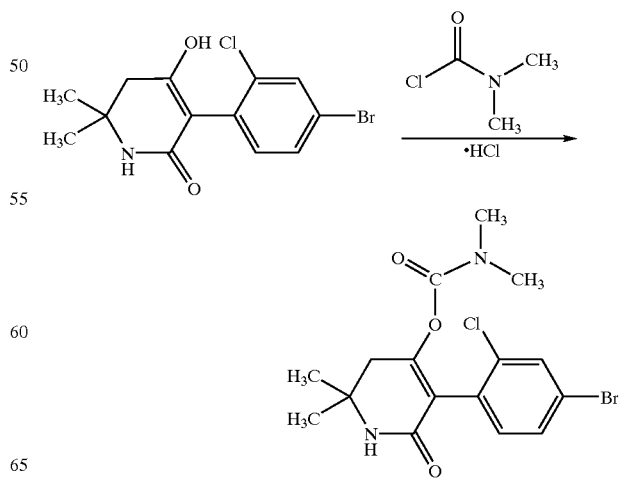

The compounds of the formula (II)

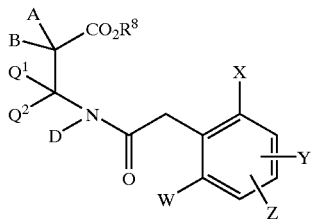
(II)

in which

A, B, D, Q$^1$, Q$^2$, W, X, Y, Z and R$^8$ are each as defined above, required as starting materials for the process (A) according to the invention are novel, except for the compounds

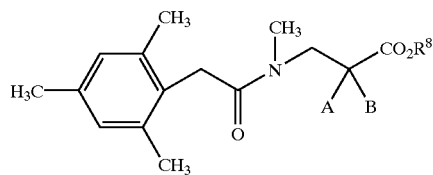

in which

A and B each represent methyl or

A and B represent —(CH$_2$)$_5$— and

R$^8$ represents alkyl.

The acylamino acid esters of the formula (II) are obtained, for example, when amino acid derivatives of the formula (XVI)

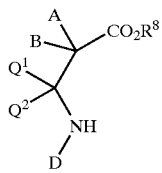
(XVI)

in which

A, B, Q$^1$, Q$^2$, R$^8$ and D are each as defined above, are acylated with substituted phenylacetyl halides of the formula (XVII)

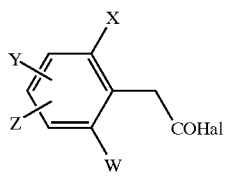
(XVII)

in which

W, X, Y and Z are each as defined above and

Hal represents chlorine or bromine, (Chem. Reviews 52, 237–416 (1953); Bhattacharya, Indian J. Chem. 6, 341–5, 1968)

or when acylamino acids of the formula (XVIII)

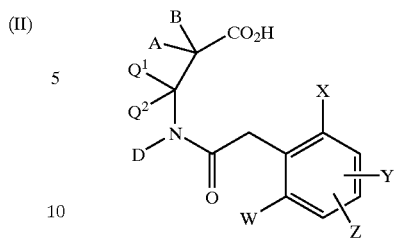
(XVIII)

in which

A, B, D, Q$^1$, Q$^2$, W, X, Y and Z are each as defined above, are esterified (Chem. Ind. (London) 1568 (1968)).

The compounds of the formula (XVIII)

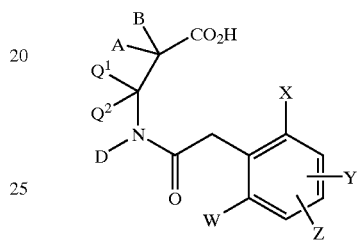
(XVIII)

in which

A, B, D, Q$^1$, Q$^2$, W, X, Y and Z are each as defined above, are novel.

The compounds of the formula (XVIII) are obtained when amino acids of the formula (XIX)

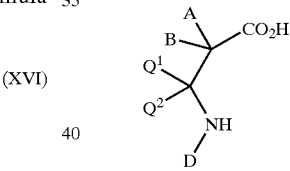
(XIX)

in which

A, B, Q$^1$, Q$^2$ and D are each as defined above, are acylated with substituted phenylacetyl halides of the formula (XVIII)

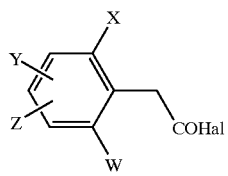
(XVII)

in which

W, X, Y and Z are each as defined above and

Hal represents chlorine or bromine, for example according to Schotten-Baumann (Organikum, VEB Deutscher Verlag der Wissenschaften, Berlin 1977, p. 505).

The compounds of the formula (XVII) are known. They can be prepared by processes known in principle (see, for example, H. Henecka, Houben-Weyl, Methoden der Organischen Chemie [Methods of organic chemistry], Vol. 8, p. 467–469 (1952)).

The compounds of the formula (XVII) are obtained, for example, by reacting substituted phenylacetic acids of the formula (XX)

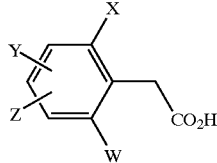
(XX)

in which

W, X, Y and Z are each as defined above, with halogenating agents (for example thionyl chloride, thionyl bromide, oxalyl chloride, phosgene, phosphorus trichloride, phosphorus tribromide or phosphorus pentachloride), if appropriate in the presence of a diluent (for example optionally chlorinated aliphatic or aromatic hydrocarbons, such as toluene or methylene chloride) at temperatures of from –20° C. to 150° C., preferably from –10° C. to 100° C.

Some of the compounds of the formulae (XVI) and (XIX) are known, and/or they can be prepared by known processes (see, for example, T. Suzuki et al., Synthetic Commun. 28, 701 (1998), R. Graf, Justus Liebigs Ann. Chem. 661, 111 (1963)).

Furthermore, the starting materials of the formula (II)

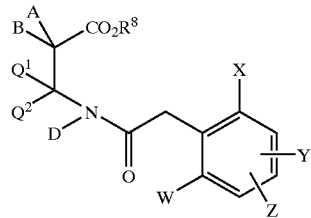
(II)

in which

A, B, D, $Q^1$, $Q^2$, W, X, Y, Z and $R^8$ are each as defined above, used in the above process (A)

can be prepared by reacting aminonitriles of the formula (XXI)

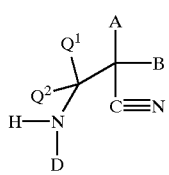
(XXI)

in which
A, B, $Q^1$, $Q^2$ and D are each as defined above,
with substituted phenylacetyl halides of the formula (XVII)

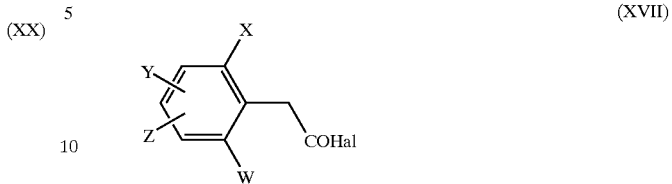
(XVII)

in which
W, X, Y, Z and Hal are each as defined above,
to give compounds of the formula (XXII)

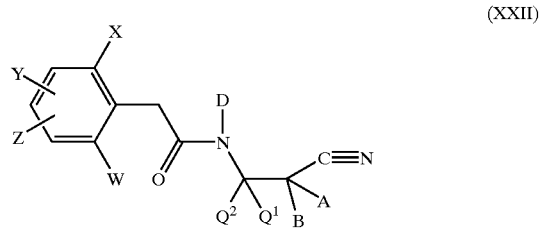
(XXII)

in which
A, B, D, $Q^1$, $Q^2$, W, X, Y and Z are each as defined above,
and then subjecting these to an acid alcoholysis.

The compounds of the formula (XXII) are likewise novel.

Some of the aminonitriles of the formula (XXI) are known, and/or they can be prepared by known processes (T. Suzuki et al., Chem. Pharm. Bull. 46, 1116 (1998)).

Some of the silylacetylenes of the formula (III) required for carrying out the process B(α) are commercially available, or they can be prepared by generally known processes. Some of the vinylstannanes of the formula (IV) required for carrying out the process B(β) are also commercially available, or they can be prepared by known processes.

Some of the boronic acids of the formula (V)

(V)

in which
Y represents optionally substituted phenyl or hetaryl,
required for carrying out the process B(γ) are commercially available, or they can be prepared in a simple manner by generally known processes.

The acid halides of the formula (VI), carboxylic anhydrides of the formula (VII), chloroformic esters or chloroformic thioesters of the formula (VIII), chloromonothioformic esters or chlorodithioformic esters of the formula (IX), sulphonyl chlorides of the formula (X), phosphorus compounds of the formula (XI) and metal hydroxides, metal alkoxides or amines of the formulae (XII) and (XIII) and isocyanates of the formula (XIV) and carbamoyl chlorides of the formula (XV) furthermore required as starting materials for carrying out the processes (C), (D), (E), (F), (G), (H) and (I) according to the invention are generally known compounds of organic or inorganic chemistry.

The process (A) is characterized in that compounds of the formula (II) in which A, B, D, $Q^1$, $Q^2$, W, X, Y, Z and $R^8$ are each as defined above are subjected to an intramolecular condensation in the presence of the base.

Suitable diluents for the process (A) according to the invention are all inert organic solvents. Preference is given to using hydrocarbons, such as toluene and xylene, furthermore ethers, such as dibutyl ether, tetrahydrofuran, dioxane, glycol dimethyl ether and diglycol dimethyl ether, moreover polar solvents, such as dimethyl sulphoxide, sulpholane, dimethylformamide and N-methyl-pyrrolidone, and also alcohols, such as methanol, ethanol, propanol, iso-propanol, butanol, iso-butanol and tert-butanol.

Suitable bases (deprotonating agents) for carrying out the process (A) according to invention are all customary proton acceptors. Preference is given to using alkali metal and alkaline earth metal oxides, hydroxides and carbonates, such as sodium hydroxide, potassium hydroxide, magnesium oxide, calcium oxide, sodium carbonate, potassium carbonate and calcium carbonate, which can also be employed in the presence of phase-transfer catalysts, such as, for example, triethylbenzyl-ammonium chloride, tetrabutylammonium bromide, Adogen 464 (=methyltrialkyl-($C_8$–$C_{10}$) ammonium chloride) or TDA 1 (=tris-(methoxyethoxyethyl)-amine). Alkali metals such as sodium and potassium can also be used. Furthermore, alkali metal and alkaline earth metal amides and hydrides, such as sodium amide, sodium hydride and calcium hydride and additionally also alkali metal alkoxides, such as sodium methoxide, sodium ethoxide and potassium tert-butoxide can be employed.

When carrying out process (A) according to the invention, the reaction temperatures can be varied within a relatively wide range. In general, the reaction is carried out at temperatures between −50° C. and 200° C., preferably between −20° C. and 150° C.

The process (A) according to the invention is generally carried out under atmospheric pressure.

When carrying out the process (A) according to the invention, the reaction components of the formula (II) and the deprotonating bases are generally employed in approximately double-equimolar amounts. However, it is also possible to use a larger excess (up to 3 mol) of one component or the other.

Suitable catalysts for carrying out the process B (α) to B (γ) according to the invention are palladium(0) complexes. Use is made, for example, of tetrakis-(triphenylphosphine) palladium. Also suitable are palladium(II) compounds, such as bis(triphenylphosphine)palladium(II) chloride.

Suitable acid acceptors for carrying out the processes B (α) and B (γ) according to the invention are inorganic or organic bases. These preferably include alkaline earth metal or alkali metal hydroxides, acetates, carbonates or bicarbonates, such as, for example, sodium hydroxide, potassium hydroxide, barium hydroxide or ammonium hydroxide, sodium acetate, potassium acetate, calcium acetate or ammonium acetate, sodium carbonate, potassium carbonate or ammonium carbonate, sodium bicarbonate or potassium bicarbonate, alkali metal fluorides, such as, for example, potassium fluoride and caesium fluoride, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Suitable diluents for carrying out the process B (γ) according to the invention are water, organic solvents and any mixtures thereof. Organic solvents which may be mentioned in an exemplary manner for processes B (α) to B (γ) are: aliphatic, alicyclic or aromatic hydrocarbons, such as, for example, petroleum ether, hexane, heptane, cyclohexane, methylcyclohexane, benzene, toluene, xylene or decaline; halogenated hydrocarbons, such as, for example, chlorobenzene, dichlorobenzene, methylene chloride, chloroform, carbon tetrachloride, dichloroethane, trichloroethane or tetrachloroethylene; ethers, such as diethyl ether, diisopropyl ether, methyl tert-butyl ether, methyl tert-amyl ether, dioxane, tetrahydrofuran, 1,2-dimethoxyethane, 1,2-diethoxyethane, diethylene glycol dimethyl ether or anisol; alcohols, such as methanol, ethanol, n- or iso-propanol, n-, iso-, sec or tert-butanol, ethanediol, propane-1,2-diol, ethoxyethanol, methoxyethanol, diethylene glycol monomethyl ether; diethylene glycol monoethyl ether; water.

When carrying out the process (B) according to the invention, the reaction temperature can be varied within a relatively wide range. In general, the reaction is carried out at temperatures between 0° C. and +180° C., preferably between +50° C. and +150° C.

When carrying out the process B (α), silylacetylenes of the formula (III) and compounds of the formulae (I-a) to (I-g) are employed in a molar ratio of from 1:1 to 10:1, preferably from 1:1 to 3:1. When carrying out the process B(β), vinylstannanes of the formula (IV) and compounds of the formulae (I-a) to (I-g) are employed in a molar ratio of from 1:1 to 10:1, preferably from 1:1 to 3:1.

When carrying out the process B (γ) according to the invention, the boronic acid of the formula (V) and the compounds of the formulae (I-a) to (I-g) are employed in a molar ratio of from 1:1 to 3:1, preferably from 1:1 to 2:1.

The catalyst is generally employed in an amount from 0.005 to 0.5 mol, preferably 0.01 mol to 0.1 mol, per mole of the compounds (I-1-a) to (I-1-g). The base is generally employed in excess.

The process (C-α) is characterized in that compounds of the formula (I-a) are in each case reacted with carbonyl halides of the formula (VI), if appropriate in the presence of a diluent and if appropriate in the presence of an acid binder.

Suitable diluents for the process (C-α) according to the invention are all solvents which are inert towards the acid halides. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such ethyl acetate nitriles, such as acetonitrile, and also strongly polar solvents, such as demethylformamide, dimethyl sulphoxide and sulpholane. The hydrolytic stability of the acid halide permitting, the reaction can also be carried out in the presence of water.

Suitable acid binders for the reaction according to the process (C-α) according to the invention are all customary acid acceptors. Preference is given to using tertiary amines, such as triethylamine, pyridine, diazabicyclooctane (DABCO), diazabicycloundecene (DBU), diazabicyclononene (DBN), Hünig base and N,N-dimethyl-aniline, further alkaline earth metal oxides, such as magnesium oxide and calcium oxide, moreover alkali metal and alkaline earth metal carbonates, such as sodium carbonate, potassium carbonate and calcium carbonate, and also alkali metal hydroxides, such as sodium hydroxide and potassium hydroxide.

The reaction temperatures in the process (C-α) according to the invention can be varied within a relatively wide range.

In general, the reaction is carried out at temperatures between −20° C. and +150° C., preferably between 0° C. and 100° C.

When carrying out the process (C-α) according to the invention, the starting materials of the formula (I-a) and the carbonyl halide of the formula (VI) are generally in each case employed in approximately equivalent amounts. However, it is also possible to employ a relatively large excess (up to 5 mol) of the carbonyl halide. Work-up is carried out by customary methods.

The process (C-β) is characterized in that compounds of the formulae (I-a) are reacted with carboxylic anhydrides of the formula (VII), if appropriate in the presence of a diluent and if appropriate in the presence of an acid binder.

Preferred diluents for the process (C-β) according to the invention are those diluents which are also preferred when acid halides are used. Otherwise, it is also possible for a carboxylic anhydride employed in excess to act simultaneously as a diluent.

In the process (C-β), acid binders which are added, if appropriate, are preferably those acid binders which are also preferred when acid halides are used.

In the process (C-β) according to the invention, the reaction temperatures can be varied within a relatively wide range. In general, the reaction is carried out at temperatures between −20° C. and +150° C., preferably between 0° C. and 100° C.

When carrying out the process (C-β) according to the invention, the starting materials of the formula (I-a) and the carboxylic anhydride of the formula (VII) are generally each employed in approximately equivalent amounts. However, it is also possible to use a relatively large excess (up to 5 mol) of the carboxylic anhydride. Work-up is carried out by customary methods.

In general, the adopted procedure is to remove diluent and excess carboxylic anhydride and also the carboxylic acid formed by distillation or by washing with an organic solvent or with water.

The process (D) is characterized in that compounds of the formula (I-a) are in each case reacted with chloroformic esters or chloroformic thioesters of the formula (VIII), if appropriate in the presence of a diluent and if appropriate in the presence of an acid binder.

Suitable acid binders for the reaction according to the process (D) according to the invention are all customary acid acceptors. Preference is given to using tertiary amines, such as triethylamine, pyridine, DABCO, DBU, DBA, Hünig base and N,N-dimethyl-aniline, furthermore alkaline earth metal oxides, such as magnesium oxide and calcium oxide, moreover alkali metal carbonates and alkaline earth metal carbonates, such as sodium carbonate, potassium carbonate and calcium carbonate, and also alkali metal hydroxides, such as sodium hydroxide and potassium hydroxide.

Suitable diluents for the process (D) according to the invention are all solvents which are inert towards the chloroformic esters or chloroformic thioesters. Preference is given to using hydrocarbons, such as benzine, benzene, toluene, xylene and tetraline, furthermore halogenated hydrocarbons, such as methylene chloride, chloroform, carbon tetrachloride, chlorobenzene and o-dichlorobenzene, moreover ketones, such as acetone and methyl isopropyl ketone, furthermore ethers, such as diethyl ether, tetrahydrofuran and dioxane, additionally carboxylic esters, such as ethyl acetate, nitriles, such as acetonitrile, and also strongly polar solvents, such as dimethylformamide, dimethyl sulphoxide and sulpholane.

When carrying out the process (D) according to the invention, the reaction temperatures can be varied within a relatively wide range. If the reaction is carried out in the presence of a diluent and an acid binder, the reaction temperatures are generally between −20° C. and +100° C., preferably between 0° C. and 50° C.

The process (D) according to the invention is generally carried out under atmospheric pressure.

When carrying out the process (D) according to the invention, the starting materials of the formula (I-a) and the appropriate chloroformic ester or chloroformic thioester of the formula (VIII) are generally in each case employed in approximately equivalent amounts. However, it is also possible to employ a relatively large excess (up to 2 mol) of one component or the other. Work-up is carried out by customary methods. In general, precipitated salts are removed and the reaction mixture that remains is concentrated by stripping the diluent.

The process (E) according to the invention is characterized in that compounds of the formula (I-a) are in each case reacted with compounds of the formula (IX) in the presence of a diluent and, if appropriate, in the presence of an acid binder.

In the preparation process (E), approximately 1 mol of chloromonothioformic ester or chlorodithioformic ester of the formula (IX) is reacted per mole of starting material of the formula (I-a), at from 0 to 120° C., preferably at from 20 to 60° C.

Suitable diluents which are added, if appropriate, are all inert polar organic solvents, such as nitriles, ethers, esters, amides, sulphones, sulphoxides, but also halogenoalkanes.

Preference is given to using acetonitrile, ethyl acetate, dimethyl sulphoxide, tetrahydrofuran, dimethylformamide or methylene chloride.

If, in a preferred embodiment, the enolate salt of the compound (I-a) is prepared by addition of strong deprotonating agents, such as, for example, sodium hydride or potassium tert-butoxide, it is not necessary to add further acid binders.

If acid binders are employed, these are customary inorganic or organic bases, for example sodium hydroxide, sodium carbonate, potassium carbonate, pyridine, triethylamine.

The reaction can be carried out at atmospheric pressure or under elevated pressure and is preferably carried out at atmospheric pressure. Work-up is carried out by customary methods.

The process (F) according to the invention is characterized in that compounds of the formula (I-a) are in each case reacted with sulphonyl chlorides of the formula (X), if appropriate in the presence of a diluent and if appropriate in the presence of an acid binder.

In the preparation process (F), approximately 1 mol of sulphonyl chloride of the formula (X) is reacted per mole of starting material of the formula (I-a), at from −20 to 150° C., preferably at from 20 to 70° C.

Suitable diluents which are added, if appropriate, are all inert polar organic solvents, such as esters, ethers, amides, nitrites, sulphones, sulphoxides or halogenated hydrocarbons, such as methylene chloride.

Preference is given to using acetonitrile, ethyl acetate, dimethyl sulphoxide, tetrahydrofuran, dimethylformamide, methylene chloride.

If, in a preferred embodiment, the enolate salt of the compound (I-a) is prepared by addition of strong deprotonating agents (such as, for example, sodium hydride or potassium tert-butoxide), it is not necessary to add further acid binders.

If acid binders are employed, these are customary inorganic or organic bases, for example sodium hydroxide, sodium carbonate, potassium carbonate, pyridine, triethylamine.

The reaction can be carried out at atmospheric pressure or under elevated pressure and is preferably carried out at atmospheric pressure. Work-up is carried out by customary methods The process (G) according to the invention is characterized in that compounds of the formula (I-a) are in each case reacted with phosphorus compounds of the formula (XI), if appropriate in the presence of a diluent and if appropriate in the presence of an acid binder.

In the preparation process (G), 1 to 2, preferably 1 to 1.3 mol of the phosphorus compound of the formula (XI) are reacted per mole of the compound (I-a) at temperatures between −40° C. and 150° C., preferably between −10 and 110° C., to give compounds of the formula (I-e).

Suitable solvents which are added, if appropriate, are all inert polar organic solvents, such as ethers, amides, nitrites, alcohols, sulphides, sulphones, sulphoxides, etc.

Preference is given to using acetonitrile, dimethyl sulphoxide, tetrahydrofuran, dimethylformamide, methylene chloride.

Suitable acid binders which are added, if appropriate, are customary inorganic or organic bases, such as hydroxides, carbonates or amines. Examples include sodium hydroxide, sodium carbonate, potassium carbonate, pyridine, triethylamine.

The reaction can be carried out at atmospheric pressure or under elevated pressure and is preferably carried out under atmospheric pressure. Work-up is carried out by customary methods of organic chemistry. The resulting end products are preferably purified by crystallization, chromatographic purification or by so-called "incipient distillation", i.e. removal of the volatile components under reduced pressure.

The process (H) is characterized in that compounds of the formula (I-a) are reacted with metal hydroxides or metal alkoxides of the formula (XII) or amines of the formula (XIII), if appropriate in the presence of a diluent.

Preferred diluents for the process (H) according to the invention are ethers, such as tetrahydrofuran, dioxane, diethyl ether or else alcohols, such as methanol, ethanol, isopropanol, but also water.

The process (H) according to the invention is generally carried out under atmospheric pressure.

The reaction temperatures are generally between −20° C. and 100° C., preferably between 0° C. and 50° C.

The process (I) according to the invention is characterized in that compounds of the formula (I-a) are in each case reacted with (I-α) compounds of the formula (XIV), if appropriate in the presence of a diluent and if appropriate in the presence of a catalyst, or (I-β) with compounds of the formula (XV), if appropriate in the presence of a diluent and if appropriate in the presence of an acid binder.

In the preparation process (I-α), approximately 1 mol of isocyanate of the formula (XIV) is reacted per mole of starting material of the formula (I-a), at from 0 to 100° C., preferably at from 20 to 50° C.

Suitable diluents which are added, if appropriate, are all inert organic solvents, such as nitrites, esters, ethers, amides, sulphones, sulphoxides.

If appropriate, catalysts may be added to accelerate the reaction. Very advantageously, the catalysts which are employed are organotin compounds, such as, for example, dibutyltin dilaurate. The reaction is preferably carried out at atmospheric pressure.

In the preparation process (I-β), approximately 1 mol of carbamoyl chloride of the formula (XV) is reacted per mole of starting material of the formula (I-a), at from −20 to 150° C., preferably at from 0 to 70° C.

Suitable diluents which are added, if appropriate, are all inert polar organic solvents, such as nitrites, esters, ethers, amides, sulphones, sulphoxides or halogenated hydrocarbons.

Preference is given to using acetonitrile, ethylene acetate, dimethyl sulphoxide, tetrahydrofuran, dimethylformamide or methylene chloride.

If, in a preferred embodiment, the enolate salt of the compound (Ia) is prepared by addition of strong deprotonating agents (such as, for example, sodium hydride or potassium tert-butoxide), it is not necessary to add further acid binders.

If acid binders are employed, these are customary inorganic or organic bases, for example sodium hydroxide, sodium carbonate, potassium carbonate, triethylamine or pyridine.

The reaction can be carried out at atmospheric pressure or under elevated pressure and is preferably carried out at atmospheric pressure. Work-up is carried out by customary methods.

The active compounds are suitable for controlling animal pests, in particular insects, arachnids and nematodes found in agriculture, in forests, in the protection of stored products and materials and in the hygiene sector, and they are tolerated well by plants and have favourable homeotherm toxicity. They are preferably employed as crop protection agents. They are active against normally sensitive and resistant species, and against all or individual developmental stages. The above-mentioned pests include:

From the order of the Isopoda, for example, *Oniscus asellus, Armadillidium vulgare, Porcellio scaber.*

From the order of the Diplopoda, for example, *Blaniulus guttulatus.*

From the order of the Chilopoda, for example, *Geophilus carpophagus, Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Aeheta domesticus, Gryllotalpa* spp., *Locusta migratoria migratorioides, Melanoplus* spp., *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp., *Damalinia* spp.

From the order of the Thysanoptera, for example, *Hercinothrips femoralis, Thrips tabaci, Thrips palmi, Frankliniella occidentalis.*

From the order of the Heteroptera, for example, *Eurygaster* spp., *Dysdercus intermedius, Piesma quadrata, Cimex lectularius, Rhodnius prolixus, Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp. *Phorodon humuli, Rhopalosiphum padi, Empoasca* spp., *Euscelis bilobatus, Nephotettix*

*cincticeps, Lecanium corni, Saissetia oleae, Laodelphax striatellus, Nilaparvata lugens, Aonidiella aurantii, Aspidiotus hederae, Pseudococcus* spp., *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicac, Panolis flammea, Spodoptera* spp., *Trichoplusia ni, Carpocapsa pomonella, Pieris* spp., *Chilo* spp., *Pyrausta nubilalis, Ephestia kuchniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp., *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phacdon cochleariae, Diabrotica* spp., *Psylliodes chrysocephala, Epilachna varivestis, Atornaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica, Lissorhoptrus oryzophilus.*

From the order of the Hymenoptera, for example, *Diprion* spp., *Hoplocampa* spp., *Lasius* spp., *Monomorium pharaonis, Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp., *Liriomyza* spp.

From the order of the Siphonaptera, for example, *Xenopsylla cheopis, Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., *Brevipalpus* spp.

The plant-parasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp., *Bursaphelenchus* spp.

At certain concentrations or application rates, the compounds according to the invention can, if appropriate, also be employed as herbicides and microbicides, for example as fungicides, antimycotics and bactericides. If appropriate, they can also be used as intermediates or precursors for the synthesis of further active compounds.

The active compounds can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are:

for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

The active compound according to the invention can be present in its commercially available formulations and in the use forms, prepared from these formulations, as a mixture with other active compounds, such as insecticides, attractants, sterilants, bactericides, acaricides, nematicides, fungicides, growth-regulating substances or herbicides. The insecticides include, for example, phosphates, carbamates, carboxylates, chlorinated hydrocarbons, phenylureas and substances produced by microorganisms.

Examples of particularly advantageous mixing components are the following:

Fungicides
- aldimorph, ampropylfos, ampropylfos potassium, andoprim, anilazine, azaconazole, azoxystrobin,
- benalaxyl, benodanil, benomyl, benzamacril, benzamacril-isobutyl, bialaphos, binapacryl, biphenyl, bitertanol, blasticidin-S, bromuconazole, bupirimate, buthiobate,
- calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
- debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
- edifenphos, epoxiconazole, etaconazole, ethirimol, etridiazole,
- famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox,
- guazatine,
- hexachlorobenzene, hexaconazole, hymexazole,
- imazalil, imibenconazole, iminoctadine, iminoctadine albesilate, iminoctadine triacetate, iodocarb, ipconazole, iprobenfos (IBP), iprodione, irumamycin,
- isoprothiolane, isovaledione,
- kasugamycin, kresoxim-methyl, copper preparations, such as: copper hydroxide, copper naphthenate, copper oxychloride, copper sulphate, copper oxide, oxine-copper and Bordeaux mixture,
- mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
- nickel dimethyldithiocarbamate, nitrothal-isopropyl, nuarimol,
- ofurace, oxadixyl, oxamocarb, oxolinic acid, oxycarboxim, oxyfenthiin,
- paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur,
- quinconazole, quintozene (PCNB),
- sulphur and sulphur preparations,
- tebuconazole, tecloftalam, tecnazene, tetcyclacis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole,
- uniconazole,
- validamycin A, vinclozolin, viniconazole,
- zarilamide, zineb, ziram and also
- Dagger G,
- OK-8705,
- OK-8801,
- α-(1,1-dimethylethyl)-β-(2-phenoxyethyl)-1H-1,2,4-triazole-1-ethanol,
- α-(2,4-dichlorophenyl)-β-fluoro-β-propyl-1H-1,2,4-triazole-1-ethanol,
- α-(2,4-dichlorophenyl)-β-methoxy-α-methyl-1H-1,2,4-triazole-1-ethanol,
- α-(5-methyl-1,3-dioxan-5-yl)-β-[[4-(trifluoromethyl)-phenyl]-methylene]-1H-1,2,4-triazole-1-ethanol,
- (5RS,6RS)-6-hydroxy-2,2,7,7-tetramethyl-5-(1H-1,2,4-triazol-1-yl)-3-octanone,
- (E)-α-(methoxyimino)-N-methyl-2-phenoxy-phenylacetamide,
- 1-isopropyl {2-methyl-1-[[[1-(4-methylphenyl)-ethyl]-amino]-carbonyl]-propyl}-carbamate,
- 1-(2,4-dichlorophenyl)-2-(1H-1,2,4-triazol-1-yl)-ethanone O-(phenylmethyl)-oxime,
- 1-(2-methyl-1-naphthalenyl)-1H-pyrrole-2,5-dione,
- 1-(3,5-dichlorophenyl)-3-(2-propenyl)-2,5-pyrrolidinedione,
- 1-[(diiodomethyl)-sulphonyl]-4-methyl-benzene,
- 1-[[2-(2,4-dichlorophenyl)-1,3-dioxolan-2-yl]-methyl]-1H-imidazole,
- 1-[[2-(4-chlorophenyl)-3-phenyloxiranyl]-methyl]-1H-1,2,4-triazole,
- 1-[1-[2-[(2,4-dichlorophenyl)-methoxy]-phenyl]-ethenyl]-1H-imidazole,
- 1-methyl-5-nonyl-2-(phenylmethyl)-3-pyrrolidinole,
- 2',6'-dibromo-2-methyl-4'-trifluoromethoxy-4'-trifluoromethyl-1,3-thiazole-5-carboxanilide,
- 2,2-dichloro-N-[1-(4-chlorophenyl)-ethyl]-1-ethyl-3-methyl-cyclopropane-carboxamide,
- 2,6-dichloro-5-(methylthio)-4-pyrimidinyl-thiocyanate,
- 2,6-dichloro-N-(4-trifluoromethylbenzyl)-benzamide,
- 2,6-dichloro-N-[[4-(trifluoromethyl)-phenyl]-methyl]-benzamide,
- 2-(2,3,3-triiodo-2-propenyl)-2H-tetrazole,
- 2-[(1-methylethyl)-sulphonyl]-5-(trichloromethyl)-1,3,4-thiadiazole,
- 2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
- 2-aminobutane,
- 2-bromo-2-(bromomethyl)-pentanedinitrile,
- 2-chloro-N-(2,3-dihydro-1,1,3-trimethyl-1H-inden-4-yl)-3-pyridinecarboxamide,
- 2-chloro-N-(2,6-dimethylphenyl)-N-(isothiocyanatomethyl)-acetamide,
- 2-phenylphenol (OPP),
- 3,4-dichloro-1-[4-(difluoromethoxy)-phenyl]-1H-pyrrole-2,5-dione,
- 3,5-dichloro-N-[cyano[(1-methyl-2-propinyl)-oxy]-methyl]-benzamide,
- 3-(1,1-dimethylpropyl-1-oxo-1H-indene-2-carbonitrile,
- 3-[2-(4-chlorophenyl)-5-ethoxy-3-isoxazolidinyl]-pyridine,
- 4-chloro-2-cyano-N,N-dimethyl-5-(4-methylphenyl)-1H-imidazole-1-sulphonamide,
- 4-methyl-tetrazolo[1,5-a]quinazolin-5(4H)-one,
- 8-(1,1-dimethylethyl)-N-ethyl-N-propyl-1,4-dioxaspiro[4.5]decane-2-methanamine,
- 8-hydroxyquinoline sulphate,
- 9H-xanthene-2-[(phenylamino)-carbonyl]-9-carboxylic hydrazide,
- bis-(1-methylethyl)-3-methyl-4-[(3-methylbenzoyl)-oxy]-2,5-thiophenedicarboxylate,
- cis-1-(4-chlorophenyl)-2-(1H-1,2,4-triazol-1-yl)-cycloheptanol, cis-4-[3-[4-(1,1-dimethylpropyl)-phenyl-2-methylpropyl]-2,6-dimethyl-morpholine-hydrochloride,
ethyl [(4-chlorophenyl)-azo]-cyanoacetate,
potassium hydrogen carbonate,
methanetetrathiol sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy-3-pyridinyl)-cyclopropanecarboxamide,
N-[2,2,2-trichloro-1-[(chloroacetyl)-amino]-ethyl]-benzamide,
N-[3-chloro-4,5-bis-(2-propinyloxy)-phenyl]-N'-methoxy-methanimidamide,
N-formyl-N-hydroxy-DL-alanine sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran]-3'-one,
Bactericides
  bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.
Insecticides/Acaricides/Nematicides
  abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,
  *Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine,
deltamethrin, demeton M, demeton S, demeton-S-methyl, diafenthiuron, diazinon, dichlorvos, diflubenzuron, dimethoat, dimethylvinphos, diofenolan, disulfoton, docusat-sodium, dofenapyn,
eflusilanate, emamectin, empenthrin, endosulfan, *Entomopfthora* spp., esfenvalerate, ethiofencarb, ethion, ethoprophos, etofenprox, etoxazole, etrimfos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb,
granulosis viruses,
halofenozide, HCH, heptenophos, hexaflumuron, hexythiazox, hydroprene,
imidacloprid, isazofos, isofenphos, isoxathion, ivermectin,
lambda-cyhalothrin, lufenuron,
malathion, mecarbam, metaldehyde, methamidophos, *Metharhizium anisopliae, Metharhizium flavoviride*, methidathion, methiocarb, methomyl, methoxyfenozide, metolcarb, metoxadiazone, mevinphos, milbemectin, monocrotophos,
naled, nitenpyram, nithiazine, novaluron, nuclear polyhedrosis viruses,
omethoat, oxamyl, oxydemethon M,
*Paecilomyces fumosoroseus*, parathion A, parathion M, permethrin, phenthoat, phorat, phosalone, phosmet, phosphamidon, phoxim, pirimicarb, pirimiphos A, pirimiphos M, profenofos, promecarb, propoxur, prothiofos, prothoat, pymetrozine, pyraclofos, pyresmethrin, pyrethrum, pyridaben, pyridathion, pyrimidifen, pyriproxyfen,
quinalphos,
ribavirin,
salithion, sebufos, silafluofen, spinosad, sulfotep, sulprofos,
tau-fluvalinate, tebufenozide, tebufenpyrad, tebupirimiphos, teflubenzuron, tefluthrin, temephos, temivinphos, terbufos, tetrachlorvinphos, theta-cypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb,
vamidothion, vaniliprole, *Verticillium lecanii,*
YI 5302
zeta-cypermethrin, zolaprofos
(1R-cis)-[5-(phenylmethyl)-3-furanyl]-methyl-3-[(dihydro-2-oxo-3(2H)-furanylidene)-methyl]-2,2-dimethylcyclopropane carboxylate
(3-phenoxyphenyl)-methyl-2,2,3,3-tetramethylcyclopropane carboxylate
1-[(2-chloro-5-thiazolyl)methyl]tetrahydro-3,5-dimethyl-N-nitro-1,3,5-triazine-2(1H)-imine
2-(2-chloro-6-fluorophenyl)-4-[4-(1,1-dimethylethyl)phenyl]-4,5-dihydro-oxazole
2-(acetlyoxy)-3-dodecyl-1,4-naphthalenedione
2-chloro-N-[[[4-(1-phenylethoxy)-phenyl]-amino]-carbonyl]-benzamide
2-chloro-N-[[[4-(2,2-dichloro-1,1-difluoroethoxy)-phenyl]-amino]-carbonyl]-benzamide
3-methylphenyl propylcarbamate
4-[4-(4-ethoxyphenyl)-4-methylpentyl]-1-fluoro-2-phenoxy-benzene
4-chloro-2-(1,1-dimethylethyl)-5-[[2-(2,6-dimethyl-4-phenoxyphenoxy)ethyl]thio]-3(2H)-pyridazinone
4-chloro-2-(2-chloro-2-methylpropyl)-5-[(6-iodo-3-pyridinyl)methoxy]-3(2H)-pyridazinone
4-chloro-5-[(6-chloro-3-pyridinyl)methoxy]-2-(3,4-dichlorophenyl)-3(2H)-pyridazinone
*Bacillus thuringiensis* strain EG-2348
[2-benzoyl-1-(1,1-dimethylethyl)-hydrazinobenzoic acid
2,2-dimethyl-3-(2,4-dichlorophenyl)-2-oxo-1-oxaspiro[4.5]dec-3-en-4-yl butanoate

[3-[(6-chloro-3-pyridinyl)methyl]-2-thiazolidinylidene]-cyanamide
dihydro-2-(nitromethylene)-2H-1,3-thiazine-3(4H)-carboxaldehyde
ethyl [2-[[1,6-dihydro-6-oxo-1-(phenylmethyl)-4-pyridazinyl]oxy]ethyl]-carbamate
N-(3,4,4-trifluoro-1-oxo-3-butenyl)-glycine
N-(4-chlorophenyl)-3-[4-(difluoromethoxy)phenyl]-4,5-dihydro-4-phenyl-1H-pyrazole-1-carboxamide
N-[(2-chloro-5-thiazolyl)methyl]-N'-methyl-N''-nitro-guanidine
N-methyl-N'-(1-methyl-2-propenyl)-1,2-hydrazinedicarbothioamide
N-methyl-N'-2-propenyl-1,2-hydrazinedicarbothioamide
O,O-diethyl [2-(dipropylamino)-2-oxoethyl]-ethylphosphoramidothioate.

Mixtures with other known active compounds such as herbicides or with fertilizers and growth regulators are also possible.

When used as insecticides, the active compounds according to the invention can furthermore be present in their commercially available formulations and in the use forms, prepared from these formulations, as a mixture with synergists. Synergists are compounds which increase the action of the active compounds, without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and stored-product pests, the active compound is distinguished by an excellent residual action on wood and clay as well as good stability to alkali on limed substrates.

The active compounds according to the invention are not only active against plant pests, hygiene pests and stored-product pests, but also, in the veterinary medicine sector, against animal parasites (ectoparasites) such as hard ticks, soft ticks, mange mites, harvest mites, flies (stinging and licking), parasitizing fly larvae, lice, hair lice, bird lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp., *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis, Periplaneta americana, Blattela germanica, Supella* spp.

From the subclass of the Acaria (Acarida) and the orders of the Meta- and Mesostigmata, for example, *Argas* spp., *Omithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds according to the invention are also suitable for controlling arthropods which attack agricultural livestock such as, for example, cattle, sheep, goats, horses, pigs, donkeys, camels, buffaloes, rabbits, chickens, turkeys, ducks, geese, honey-bees, other domestic animals such as, for example, dogs, cats, caged birds, aquarium fish and so-called experimental animals such as, for example, hamsters, guinea pigs, rats and mice. By controlling these arthropods, cases of death and reductions in productivity (for meat, milk, wool, hides, eggs, honey and the like) should be diminished, so that more economical and simpler animal husbandry is possible by the use of the active compounds according to the invention.

The active compounds according to the invention are used in the veterinary sector in a known manner by enteral administration in the form of, for example, tablets, capsules, potions, drenches, granules, pastes, boluses, the feed-through method, suppositories, by parenteral administration such as, for example, by injections (intramuscularly, subcutaneously, intravenously, intraperitoneally and the like), implants, by nasal administration, by dermal administration in the form of, for example, immersing or dipping, spraying, pouring-on, spotting-on, washing, dusting, and with the aid of active-compound-comprising moulded articles such as collars, ear tags, tail tags, limb bands, halters, marking devices and the like.

When used for cattle, poultry, domestic animals and the like, the active compounds can be applied as formulations (for example powders, emulsions, flowables) comprising the active compounds in an amount of 1 to 80% by weight, either directly or after 100- to 10000-fold dilution, or they may be used as a chemical dip.

Moreover, it has been found that the active compounds according to the invention show a potent insecticidal action against insects which destroy industrial materials.

The following insects may be mentioned by way of example and with preference, but not by way of limitation:

Beetles such as

*Hylotrupes bajulus, Chlorophorus pilosis, Anobium punctatum, Xestobium rufovillosum, Ptilinus pecticomis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec., *Tryptodendron* spec., *Apate monachus, Bostrychus capucins, Heterobostrychus brunneus, Sinoxylon* spec., *Dinoderus minutus.*

Dermapterans such as
*Sirex juvencus, Urocerus gigas, Urocerus gigas taignus, Urocerus augur.*
Termites such as
*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*
Bristle-tails such as *Lepisma saccharina.*

Industrial materials in the present context are understood as meaning non-living materials such as, preferably, polymers, adhesives, glues, paper and board, leather, wood, timber products and paints.

The material which is to be protected from insect attack is very especially preferably wood and timber products.

Wood and timber products which can be protected by the composition according to the invention, or mixtures comprising it, are to be understood as meaning, for example:

Construction timber, wooden beams, railway sleepers, bridge components, jetties, vehicles made of wood, boxes, pallets, containers, telephone poles, wood lagging, windows and doors made of wood, plywood, chipboard, joinery, or timber products which quite generally are used in house construction or building joinery.

The active compounds can be used as such, in the form of concentrates or generally customary formulations such as powders, granules, solutions, suspensions, emulsions or pastes.

The above-mentioned formulations can be prepared in a manner known per se, for example by mixing the active compounds with at least one solvent or diluent, emulsifier, dispersant and/or binder or fixative, water repellant, if desired desiccants and UV stabilizers, and if desired colorants and pigments and other processing auxiliaries.

The insecticidal compositions or concentrates used for protecting wood and timber products comprise the active compound according to the invention in a concentration of 0.0001 to 95% by weight, in particular 0.001 to 60% by weight.

The amount of composition or concentrate employed depends on the species and the abundance of the insects and on the medium. The optimal quantity to be employed can be determined in each case by test series upon application. In general, however, it will suffice to employ 0.0001 to 20% by weight, preferably 0.001 to 10% by weight, of the active compound, based on the material to be protected.

A suitable solvent and/or diluent is an organochemical solvent or solvent mixture and/or an oily or oil-type organochemical solvent or solvent mixture of low volatility and/or a polar organochemical solvent or solvent mixture and/or water and, if appropriate, an emulsifier and/or wetter.

Organochemical solvents which are preferably employed are oily or oil-type solvents with an evaporation number of above 35 and a flash point of above 30° C., preferably above 45° C. Such oily and oil-type solvents which are insoluble in water and of low volatility and which are used are suitable mineral oils or their aromatic fractions or mineral-oil-containing solvent mixtures, preferably white spirit, petroleum and/or alkylbenzene.

Mineral oils with a boiling range of 170 to 220° C., white spirit with a boiling range of 170 to 220° C., spindle oil with a boiling range of 250 to 350° C., petroleum and aromatics with a boiling range of 160 to 280° C., oil of terpentine, and the like are advantageously used.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloronaphthalene, preferably α-monochloronaphthalene are used.

The organic oily or oil-type solvents of low volatility and with an evaporation number of above 35 and a flash point of above 30° C., preferably above 45° C., can be replaced in part by organochemical solvents of high or medium volatility, with the proviso that the solvent mixture also has an evaporation number of above 35 and a flash point of above 30° C., preferably above 45° C., and that the insecticide-fungicide mixture is soluble or emulsifiable in this solvent mixture.

In a preferred embodiment, some of the organochemical solvent or solvent mixture is replaced by an aliphatic polar organochemical solvent or solvent mixture. Aliphatic organochemical solvents which contain hydroxyl and/or ester and/or ether groups are preferably used, such as, for example, glycol ethers, esters or the like.

Organochemical binders used for the purposes of the present invention are the synthetic resins and/or binding drying oils which are known per se and which can be diluted in water and/or dissolved or dispersed or emulsified in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin such as indene/coumarone resin, silicone resin, drying vegetable and/or drying oils and/or physically drying binders based on a natural and/or synthetic resin.

The synthetic resin employed as binder can be employed in the form of an emulsion, dispersion or solution. Bitumen or bituminous substances may also be used as binders, in amounts of up to 10% by weight. In addition, colorants, pigments, water repellants, odour-masking agents, and inhibitors or anticorrosive agents and the like, all of which are known per se, can be employed.

In accordance with the invention, the composition or the concentrate preferably comprises, as organochemical binders, at least one alkyd resin or modified alkyd resin and/or a drying vegetable oil. Alkyd resins which are preferably used in accordance with the invention are those with an oil content of over 45% by weight, preferably 50 to 68% by weight.

Some or all of the above-mentioned binder can be replaced by a fixative (mixture) or plasticizer (mixture). These additives are intended to prevent volatilization of the active compounds, and also crystallization or precipitation. They preferably replace 0.01 to 30% of the binder (based on 100% of binder employed).

The plasticizers are from the chemical classes of the phthalic esters, such as dibutyl phthalate, dioctyl phthalate or benzyl butyl phthalate, phosphoric esters such as tributyl phosphate, adipic esters such as di-(2-ethylhexyl)-adipate, stearates such as butyl stearate or amyl stearate, oleates such as butyl oleate, glycerol ethers or higher-molecular-weight glycol ethers, glycerol esters and p-toluenesulphonic esters.

Fixatives are based chemically on polyvinyl alkyl ethers such as, for example, polyvinyl methyl ether, or ketones such as benzophenone and ethylenebenzophenone.

Other suitable solvents or diluents are, in particular, water, if appropriate as a mixture with one or more of the above-mentioned organochemical solvents or diluents, emulsifiers and dispersants.

Particularly effective timber protection is achieved by industrial-scale impregnating processes, for example the vacuum, double-vacuum or pressure processes.

The ready-to-use compositions can also comprise other insecticides, if appropriate, and also one or more fungicides, if appropriate.

Possible additional mixing components are, preferably, the insecticides and fungicides mentioned in WO 94/29 268. The compounds mentioned in this document are an explicit constituent of the present application.

Especially preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyfenozide and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The combinations according to the invention can at the same time be employed for protecting objects which come into contact with saltwater or brackish water, such as hulls, screens, nets, buildings, moorings and signalling systems, against fouling.

Fouling by sessile Oligochaeta, such as Serpulidae, and by shells and species from the Ledamorpha group (goose barnacles), such as various *Lepas* and *Scalpellum* species, or by species from the Balanomorpha group (acorn barnacles), such as *Balanus* or *Pollicipes* species, increases the frictional drag of ships and, as a consequence, leads to a marked increase in operation costs owing to higher energy consumption and additionally frequent residence in the dry dock.

Apart from fouling by algae, for example *Ectocarpus* sp. and *Ceramium* sp., fouling by sessile Entomostraka groups, which come under the generic term Cirripedia (cirriped crustaceans), is of particular importance.

Surprisingly, it has now been found that the combinations according to the invention, alone or in combination with other active compounds, have an outstanding anti-fouling action.

Using the combinations according to the invention, alone or in combination with other active compounds, allows the use of heavy metals such as, for example, in bis(trialkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylene-bisthiocarbamate, zinc dimethyldithiocarbamate, zinc ethylenebisthiocarbamate, zinc salts and copper salts of 2-pyridinethiol 1-oxide, bis-dimethyldithiocarbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:
algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;
fungicides such as
benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;
molluscicides such as
fentin acetate, metaldehyde, methiocarb, niclosamid, thiodicarb and trimethacarb;
or conventional antifouling active compounds such as
4,5-dichloro-2-octyl-4-isothiazolin-3-one, diiodomethylparatryl sulfone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulfonyl)-pyridine, 2,4,5,6-tetrachloroisophthalonitrile, tetra-methylthiuram disulfide and 2,4,6-trichlorophenylmaleiimide.

The antifouling compositions used comprise the active compound according to the invention of the compositions according to the invention in a concentration of 0.001 to 50% by weight, in particular 0.01 to 20% by weight.

Moreover, the antifouling compositions according to the invention comprise the customary components such as, for example, those described in Ungerer, Chem. Ind. 1985, 37, 730–732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/styrene/acrylonitrile rubbers, drying oils such as linseed oil, resin esters or modified hardened resins in combination with tar or bitumens, asphalt and epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the rheological properties and other conventional constituents. The compounds according to the invention or the above-mentioned mixtures may also be incorporated into self-polishing antifouling systems.

The active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and excipients in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

In the field of household insecticides, they are used alone or in combination with other suitable active compounds, such as phosphoric acid esters, carbamates, pyrethroids, growth regulators or active compounds from other known classes of insecticides.

They are used as aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for spreading or in bait stations.

The active compounds according to the invention can be used as defoliants, desiccants, haulm killers and, especially, as weed killers. Weeds in the broadest sense are understood to mean all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: *Abutilon, Amaranthus, Ambrosia, Anoda, Anthemis, Aphanes, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindemia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium*.

Dicotyledonous crops of the genera: *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*.

Monocotyledonous weeds of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum*.

Monocotyledonous crops of the genera: *Allium, Ananas, Asparagus, Avena, Hordeum, Oryza, Panicum, Saccharum, Secale, Sorghum, Triticale, Triticum, Zea*.

However, the use of the active compounds according to the invention is in no way restricted to these genera, but also extends in the same manner to other plants.

The active compounds according to the invention are suitable, depending on the concentration, for the total control of weeds, for example on industrial terrain and rail tracks, and on paths and areas with and without tree plantings. Similarly, the active compounds according to the invention can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds according to the invention have strong herbicidal activity and a broad active spectrum when used on the soil and on above-ground parts of plants. To a certain extent they are also suitable for the selective control of monocotyledonous and dicotyledonous weeds in monocotyledonous and dicotyledonous crops, both by the pre-emergence and by the post-emergence method.

At certain concentrations or application rates, the active compounds according to the invention can also be employed for controlling animal pests and fungal or bacterial plant diseases. If appropriate, they can also be used as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant varieties protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on and, in the case of propagation material, in particular in the case of seeds, also by applying one or more coats.

As already mentioned above, it is possible to treat all plants and their parts according to the invention. In a preferred embodiment, wild plant species and plant varieties, or those obtained by conventional biological breeding, such as crossing or protoplast fusion, and parts thereof, are treated. In a further preferred embodiment, transgenic plants and plant varieties obtained by genetical engineering, if appropriate in combination with conventional methods (Genetically Modified Organisms), and parts thereof are treated. The term "parts" or "parts of plants" or "plant parts" has been explained above.

Particularly preferably, plants of the plant varieties which are in each case commercially available or in use are treated according to the invention. Plant varieties are to be understood as meaning plants having certain properties ("traits") and which have been obtained by conventional breeding, by mutagenesis or by recombinant DNA techniques. They can be varieties, bio- or genotypes.

Depending on the plant species or plant varieties, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which exceed the effects which were actually to be expected.

The transgenic plants or plant varieties (i.e. those obtained by genetical engineering) which are preferably treated according to the invention include all plants which, in the genetic modification, received genetic material which imparted particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapes), and particular emphasis is given to maize, soya beans, potatoes, cotton and oilseed rape. Traits that are emphasized are in particular increased defence of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c Cry2Ab, Cry3Bb and CryIF and also combinations thereof) (hereinbelow referred to as "Bt plants"). Traits that are also particularly emphasized are the increased defence of the plants to fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylurea, for example maize). Herbicide-resistant plants (plants bred in a conventional manner for herbicide tolerance) which may be mentioned include the varieties sold under the name Clearfield® (for example maize). Of course, these statements also apply to plant varieties having these genetic traits or genetic traits still to be developed, which plants will be developed and/or marketed in the future.

The plants listed can be treated according to the invention in a particularly advantageous manner with the compounds of the formula (I). The preferred ranges stated above for the active compounds also apply to the treatment of these plants. Particular emphasis is given to the treatment of plants with the mixtures specifically mentioned in the present text.

The active compounds can be converted into the customary formulations such as solutions, emulsions, wettable powders, suspensions, powders, dusts, pastes, soluble powders, granules, suspension-emulsion concentrates, natural and synthetic materials impregnated with active compound, and microencapsulations in polymeric materials.

These formulations are produced in a known manner, for example by mixing the active compounds with extenders, that is, liquid solvents and/or solid carriers, optionally with the use of surfactants, that is, emulsifiers and/or dispersants, and/or foam formers.

If the extender used is water, it is also possible, for example, to use organic solvents as cosolvents. The following are essentially suitable as liquid solvents: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water.

Suitable solid carriers are: for example ammonium salts and ground natural minerals such as kaolins, clays, talc, chalk, quartz, attapulgite, montmorillonite or diatomaceous earth, and ground synthetic materials such as highly-disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example nonionic and anionic emulsifiers such as polyoxyethylene fatty acid esters, polyoxyethylene fatty alcohol ethers, for example alkylaryl polyglycol ethers, alkylsulphonates, alkyl sulphates, aryl-sulphonates, or else protein hydrolysates; suitable dispersants are: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic colorants such alizarin colorants, azo colorants and metal phthalocyanine colorants, and trace nutrients such as salts of iron, manganese, boron, copper, cobalt, molybdenum and zinc.

The formulations generally comprise between 0.1 and 95% by weight of active compound, preferably between 0.5 and 90%.

For controlling weeds, the active compounds according to the invention, as such or in their formulations, can also be used as mixtures with known herbicides and/or substances which improve the compatibility with crop plants ("safeners"), finished formulations or tank mixes being possible. Also possible are mixtures with weed-killers comprising one or more known herbicides and a safener.

Possible components for the mixtures are known herbicides, for example
acetochlor, acifluorfen (-sodium), aclonifen, alachlor, alloxydim (-sodium), ametryne, amicarbazone, amidochlor, amidosulfuron, anilofos, asulam, atrazine, azafenidin, azimsulfuron, BAS-662H, beflubutamid, benazolin (-ethyl), benfuresate, bensulfuron (-methyl), bentazon, benzfendizone, benzobicyclon, benzofenap, benzoylprop(-ethyl), bialaphos, bifenox, bispyribac (-sodium), bromobutide, bromofenoxim, bromoxynil, butachlor, butafenacil (-allyl), butroxydim, butylate, cafenstrole, caloxydim, carbetamide, carfentrazone (-ethyl), chlomethoxyfen, chloramben, chloridazon, chlorimuron (-ethyl), chlornitrofen, chlorsulfuron, chlortoluron, cinidon (-ethyl), cinmethylin, cinosulfuron, clefoxydim, clethodim, clodinafop (-propargyl), clomazone, clomeprop, clopyralid, clopyrasulfuron (-methyl), cloransulam (-methyl), cumyluron, cyanazine, cybutryne, cycloate, cyclosulfamuron, cycloxydim, cyhalofop (-butyl), 2,4-D, 2,4-DB, desmedipham, diallate, dicamba, dichlorprop (-P), diclofop (-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron (-methyl), ethofumesate, ethoxyfen, ethoxysulfuron, etobenzanid, fenoxaprop (-P-ethyl), fentrazamide, flamprop (-isopropyl, -isopropyl-L, -methyl), flazasulfuron, florasulam, fluazifop (-P-butyl), fluazolate, flucarbazone (-sodium), flufenacet, flumetsulam, flumiclorac (-pentyl), flumioxazin, flumipropyn, flumetsulam, fluometuron, fluorochloridone, fluoroglycofen (-ethyl), flupoxam, flupropacil, flurpyrsulfuron (-methyl, -sodium), flurenol (-butyl), fluridone, fluroxypyr (-butoxypropyl, -meptyl), flurprimidol, flurtamone, fluthiacet (-methyl), fluthiamide, fomesafen, foramsulfuron, glufosinate (-ammonium), glyphosate (-isopropylammonium), halosafen, haloxyfop (-ethoxyethyl, -P-methyl), hexazinone, imazamethabenz (-methyl), imazamethapyr, imazamox, imazapic, imazapyr, imazaquin, imazethapyr, imazosulfuron, iodosulfuron (-methyl, -sodium), ioxynil, isopropalin, isoproturon, isouron, isoxaben, isoxachlortole, isoxaflutole, isoxapyrifop, lactofen, lenacil, linuron, MCPA, mecoprop, mefenacet, mesotrione, metamitron, metazachlor, methabenzthiazuron, metobenzuron, metobromuron, (alpha-) metolachlor, metosulam, metoxuron, metribuzin, metsulfuron (-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, phenmedipham, picolinafen, piperophos, pretilachlor, primisulfuron (-methyl), profluazol, prometryn, propachlor, propanil, propaquizafop, propisochlor, propoxycarbazone (-sodium), propyzamide, prosulfocarb, prosulfuron, pyraflufen (-ethyl), pyrazogyl, pyrazolate, pyrazosulfuron (-ethyl), pyrazoxyfen, pyribenzoxim, pyributicarb, pyridate, pyridatol, pyriftalid, pyriminobac (-methyl), pyrithiobac (-sodium), quinchlorac, quinmerac, quinoclamine, quizalofop(-P-ethyl, -P-tefuryl), rimsulfuron, sethoxydim, simazine, simetryn, sulcotrione, sulfentrazone, sulfometuron (-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron (-methyl), thiobencarb, tiocarbazil, tralkoxydim, triallate, triasulfuron, tribenuron (-methyl), triclopyr, tridiphane, trifluralin, trifloxysulfuron, triflusulfuron (-methyl), tritosulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or broadcasting.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention is illustrated by the examples below.

PREPARATION EXAMPLES

Example I-a-1

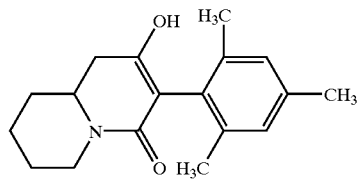

3.9 g (0.13 mol) of sodium hydride in 70 ml of absolute toluene are heated at reflux, and 33.1 g of the compound of Example II-1 in 100 ml of absolute toluene are added dropwise. The reaction is monitored by thin-layer chromatography. With ice-cooling, ethanol is added until no more hydrogen evolves, the solvent is evaporated and water is added. The toluene phase is separated off, and the aqueous phase is then acidified at 0–20° C. with concentrated hydrochloric acid and the precipitate is filtered off and dried.

The product is purified by silica gel column chromatography (dichloromethane/ethyl acetetate 3:1).

Yield: 8.41 g (30% of theory), m.p. 127° C.

Example I-a-2

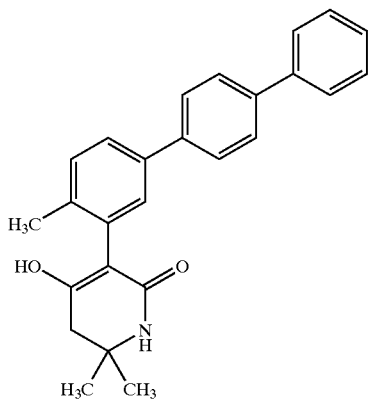

At room temperature, 3 mmol of the compound of Example I-a-4 are initially charged in 8 ml of DME (dimethoxyethane), and 6.9 ml of a 1M $NaCO_3$ solution are added. 4.5 mmol of biphenylboronic acid are added, followed by 0.15 mmol of $Pd(PPh_3)_2Cl_2$, and the mixture is stirred at room temperature for 1 h at then at 85° C. for 16 h.

Purification was carried out on silica gel using the mobile phase cyclohexane/ethyl acetate (gradient from 100:1 to 1:1).

Yield: 0.302 g (26.3% of theory), oil.

TABLE 1

The following compounds of the formula (I-a) were obtained analogously to Examples (I-a-1) and (I-a-2) and in accordance with the general statements on the preparation

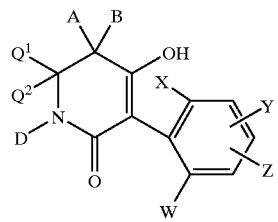

(I-a)

| Ex. No. | W | X | Y | Z | A | B | D | $Q^1$ | $Q^2$ | m.p. ° C. |
|---|---|---|---|---|---|---|---|---|---|---|
| I-a-3 | $CH_3$ | Cl | 4-Cl | H | H | H | H | $CH_3$ | $CH_3$ | 223 |
| I-a-4 | H | $CH_3$ | 5-Br | H | H | H | H | $CH_3$ | $CH_3$ | 242 |

TABLE 1-continued

The following compounds of the formula (I-a) were obtained analogously to Examples (I-a-1) and (I-a-2) and in accordance with the general statements on the preparation

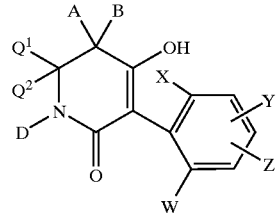

(I-a)

| Ex. No. | W | X | Y | Z | A | B | D | Q¹ | Q² | m.p. ° C. |
|---|---|---|---|---|---|---|---|---|---|---|
| I-a-5 | H | $CH_3$ | 5-(4-Cl—$C_6H_5$) | H | H | H | H | $CH_3$ | $CH_3$ | 186 |
| I-a-6 | H | $CH_3$ | 5-(2-thienyl) | H | H | H | H | $CH_3$ | $CH_3$ | oil |
| I-a-7 | H | $CH_3$ | 5-(3,5-$Cl_2$—$C_6H_3$) | H | H | H | H | $CH_3$ | $CH_3$ | oil |
| I-a-8 | H | $CH_3$ | 5-(3-Cl—$C_6H_4$) | H | H | H | H | $CH_3$ | $CH_3$ | oil |
| I-a-9 | H | $CH_3$ | 5-(3,5-$(CF_3)_2$—$C_6H_3$) | H | H | H | H | $CH_3$ | $CH_3$ | oil |
| I-a-10 | $CH_3$ | Cl | 4-Br | H | H | H | H | $CH_3$ | $CH_3$ | >245 |
| I-a-11 | $C_2H_5$ | Cl | 4-Br | H | H | H | H | $CH_3$ | $CH_3$ | 188 |
| I-a-12 | $CH_3$ | $CH_3$ | 4-$CH_3$ | H | $CH_3$ | $CH_3$ | H | H | H | 138 |
| I-a-13 | $CH_3$ | $CH_3$ | 3-$CH_3$ | 4-$CH_3$ | $CH_3$ | $CH_3$ | H | H | H | oil |
| I-a-14 | H | $CH_3$ | 5-(4-Cl—$C_6H_4$) | H | $CH_3$ | $CH_3$ | H | H | H | 214 |
| I-a-15 | $CH_3$ | $CH_3$ | 4-(4-Cl—$C_6H_4$) | H | $CH_3$ | $CH_3$ | H | H | H | 204 |
| I-a-16 | $CH_3$ | $CH_3$ | 4-$CH_3$ | H | —$(CH_2)_5$— | | H | H | H | 206 |
| I-a-17 | $CH_3$ | $CH_3$ | 3-$CH_3$ | 4-$CH_3$ | —$(CH_2)_5$— | | H | H | H | 193 |
| I-a-18 | H | $CH_3$ | 5-(4-Cl—$C_6H_4$) | H | —$(CH_2)_5$— | | H | H | H | 203 |
| I-a-19 | $CH_3$ | Cl | 4-Cl | H | $CH_3$ | $CH_3$ | H | H | H | 182 |
| I-a-20 | $CH_3$ | Cl | 4-Cl | H | —$(CH_2)_5$— | | H | H | H | 135 |
| I-a-21 | Cl | Cl | H | H | H | H | H | —$(CH_2)_4$— | H | 206 |
| I-a-22 | H | Cl | 4-Cl | H | H | H | H | —$(CH_2)_4$— | H | 182 |
| I-a-23 | $CH_3$ | $CH_3$ | 4-(4-Cl—$C_6H_4$) | H | —$(CH_2)_5$— | | H | H | H | 204 |
| I-a-24 | H | $CH_3$ | 5-(4-Cl—$C_6H_4$) | H | H | H | H | —$(CH_2)_4$— | H | 196 |
| I-a-25 | H | $CH_3$ | 5-(4-Cl—$C_6H_4$) | H | H | H | $CH_3$ | $CH_3$ | $CH_3$ | 196 |
| I-a-26 | $CH_3$ | Cl | 4-Cl | H | H | H | cyclopropyl | $CH_3$ | $CH_3$ | 191 |
| I-a-27 | $C_2H_5$ | Cl | 4-Br | H | H | H | $CH_3$ | $CH_3$ | $CH_3$ | |
| I-a-28 | $CH_3$ | Cl | 4-Cl | H | —$(CH_2)_2$—O—$(CH_2)_2$— | | H | H | H | 264 |
| I-a-29 | $CH_3$ | $CH_3$ | 4-Cl | H | —$(CH_2)_2$—O—$(CH_2)_2$— | | H | H | H | 300 |
| I-a-30 | $CH_3$ | $CH_3$ | 4-(4-Cl—$C_6H_4$) | H | H | H | —$(CH_2)_4$— | | H | 315 |
| I-a-31 | $CH_3$ | Cl | 4-Cl | H | H | H | H | —$(CH_2)_2$—O—$(CH_2)_2$— | | 311 |
| I-a-32 | H | $CH_3$ | 5-(4-Cl—$C_6H_4$) | H | H | H | H | —$(CH_2)_2$—O—$(CH_2)_2$— | | 154 |
| I-a-33 | H | $CH_3$ | 5-(4-Cl—$C_6H_4$) | H | H | H | H | —$(CH_2)_2$—$CHOCH_3$—$(CH_2)_2$— | | |
| I-a-34 | $CH_3$ | Cl | 4-Cl | H | H | H | H | —$(CH_2)_2$—$CHOCH_3$—$(CH_2)_2$— | | |

Example I-b-1

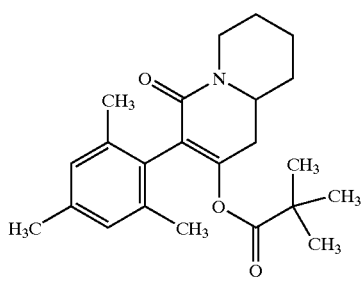

At 0–10° C., 4.95 g of the compound of Example I-a-1 in 70 ml of methyl tert-butyl ether are admixed with 1.4 ml of absolute pyridine and 2.94 ml of ethyl-diisopropylamine. 2.2 ml of pivaloyl chloride in 5 ml of methyl tert-butyl ether are then added, and the mixture is stirred at room temperature. The mixture is filtered off with suction, the residue is washed with methyl tert-butyl ether and the solution is concentrated. The reaction mixture is purified by column chromatography (cyclohexane/ethyl acetate 1:1).

Yield: 3.42 g (55% of theory), oil

TABLE 2

The following compounds of the formula (I-b) are obtained analogously to Example I-b-1 and in accordance with the general statements on the preparation

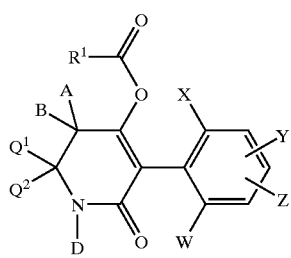

(I-b)

| Ex. No. | W | X | Y | Z | A | B | D | $Q^1$ | $Q^2$ | $R^1$ | m.p. °C. |
|---|---|---|---|---|---|---|---|---|---|---|---|
| I-b-2 | Cl | Cl | H | H | H | H | —(CH$_2$)$_4$— | | H | CH$_3$ | 124 |
| I-b-3 | Cl | Cl | H | H | H | H | —(CH$_2$)$_4$— | | H | t-C$_4$H$_9$ | 130 |
| I-b-4 | H | CH$_3$ | 5-(4-Cl—C$_6$H$_4$) | H | —(CH$_2$)$_4$— | | H | H | H | i-C$_3$H$_7$ | 183 |
| I-b-5 | H | CH$_3$ | 5-(4-Cl—C$_6$H$_4$) | H | H | H | H | CH$_3$ | CH$_3$ | i-C$_3$H$_7$ | 167 |
| I-b-6 | H | CH$_3$ | 5-(4-Cl—C$_6$H$_4$) | H | H | H | H | CH$_3$ | CH$_3$ |  | 199 |
| I-b-7 | H | CH$_3$ | 5-(4-Cl—C$_6$H$_4$) | H | H | H | H | CH$_3$ | CH$_3$ |  | 234 |
| I-b-8 | H | CH$_3$ | 5-(4-Cl—C$_6$H$_4$) | H | H | H | H | CH$_3$ | CH$_3$ |  | 178 |

Example I-c-1

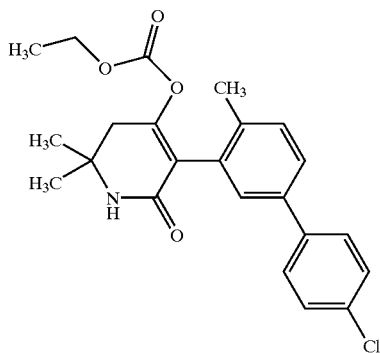

1.3 g of the compound of Example I-a-5 in 30 ml of absolute dichloromethane are, at 10–20° C., admixed with 0.42 ml of triethylamine and then with 0.3 ml of ethyl chloroformate in 2 ml of absolute dichloromethane, and the mixture is stirred at room temperature. The reaction mixture is washed twice with 10 ml of 0.5 N NaOH and the solution is dried over magnesium sulphate and concentrated using a rotary evaporator. The product is purified by silica gel colum chromatograpy (dichloromethane/ethyl acetate, 3/1).

Yield: 1.1 g (88% of theory) m.p. 195° C.

The following compounds of the formula (I-c) were obtained analogously to Example I-c-1 and in accordance with the general statements on the preparation:

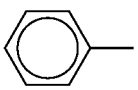

(I-c)

| Ex. No. | W | X | Y | Z | A | B | D | Q¹ | Q² | L | M | R² | m.p. °C. |
|---|---|---|---|---|---|---|---|---|---|---|---|---|---|
| I-c-2 | $CH_3$ | $CH_3$ | 4-$CH_3$ | H | $CH_3$ | $CH_3$ | H | H | H | O | O | $C_2H_5$ | 190 |
| I-c-3 | H | $CH_3$ | 5-(4-Cl—$C_6H_4$) | H | $CH_3$ | $CH_3$ | H | H | H | O | O | $C_2H_5$ | 203 |
| I-c-4 | H | $CH_3$ | 5-(4-Cl—$C_6H_5$) | H | H | H | H | $CH_3$ | $CH_3$ | O | O | 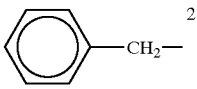 | 180 |
| I-c-5 | H | $CH_3$ | 5-(4-Cl—$C_6H_4$) | H | H | H | H | $CH_3$ | $CH_3$ | O | O | 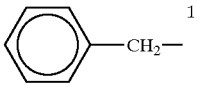 | 216 |
| I-c-6 | H | $CH_3$ | 5-(4-Cl—$C_6H_4$) | H | H | H | H | $CH_3$ | $CH_3$ | O | S | 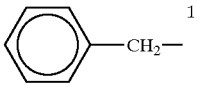 | 165–167 |

Example I-d-1

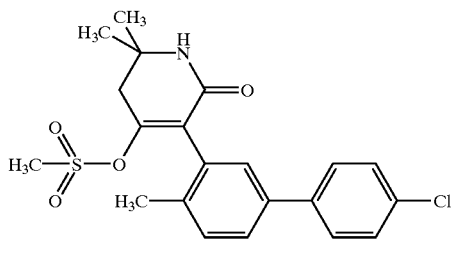

Example I-A-g-1

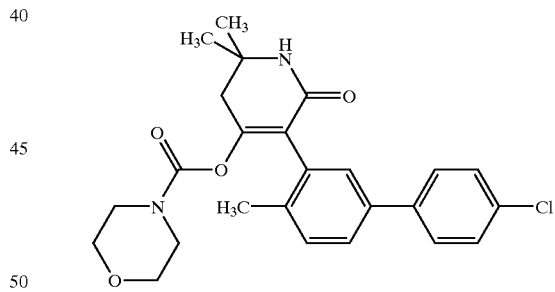

1.02 g (3 mmol) of the compound of Preparation Example I-a-5 in 10 ml of absolute dichloromethane are admixed with 0.54 ml of triethylamine. 0.26 ml (3.3 mmol) of methanesulphonyl chloride is dissolved in a little dichloromethane and added dropwise with ice-cooling. The mixture is stirred at room temperature for 2 h. The reaction solution is washed with 10% strength citric acid and extracted with dichloromethane. The organic phase is washed with 1 N NaOH solution and dried.

Yield: 1.05 g (83% of theory). m.p. 198–200° C.

1.02 g (3.0 mmol) of the compound of Preparation Example I-a-5 and 0.54 ml (3.90 mmol) of triethylamine are dissolved in 10 ml of absolute ethyl acetate and heated at reflux. 0.47 g (3.15 mmol) of morpholine-N-carbonyl chloride in 2 ml of absolute ethyl acetate is added. The mixture is heated at reflux for 2 h.

The solvent is distilled off and the residue is taken up in 50 ml of dichloromethane. The mixture is washed twice with 30 ml of semiconcentrated NaCl solution and extracted twice with 30 ml of 0.5 N NaOH solution. The organic phase is dried and concentrated. The product is purified by silica gel column chromatography (cyclohexane/ethyl acetate, 5:1→1:1). Yield 0.200 g (15% of theory), m.p. 221–223° C.

Example I-B-g-1

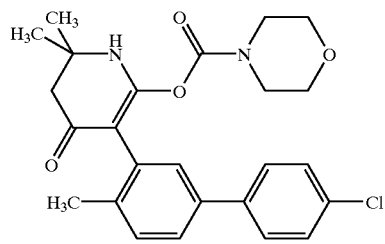

1.02 g (3.0 mmol) of the compound of Preparation Example I-a-5 and 0.54 ml (3.90 mmol) of triethylamine are dissolved in 10 ml of absolute ethyl acetate and heated at reflux. 0.47 g (3.15 mmol) of morpholin-N-carboxylic acid in 2 ml of absolute ethyl acetate are added. The mixture is heated at reflux for 2 h.

The solvent is distilled off and the residue is taken up in 50 ml of dichloromethane. The mixture is washed twice with 30 ml of semiconcentrated NaCl solution and extracted twice with 30 ml of 0.5 N NaOH solution. The organic phase is dried and concentrated. The product is purified by silica gel column chromatography (cyclohexane/ethyl acetate, 5:1→1:1). Yield 0.480 g (35% of theory), m.p. 95–97° C.

Example II-1

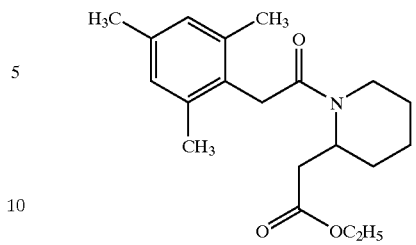

At 0–10° C., 14 ml of triethylamine are added to 17.1 g of ethyl 2-piperidinyl-acetate in 130 ml of absolute tetrahydrofuran. At room temperature, 19.7 g of mesitylene acetyl chloride in 20 ml of absolute tetrahydrofuran are then added.

The reaction solution is added to 0.5 l of ice-water and acidified with 100 ml of 1N HCl. The solution is extracted with dichloromethane, the extract is dried and the solvent is evaporated.

Yield: 33.4 g (100% of theory)

TABLE 3

The following compounds of the formula (II) are obtained analogously to Example II-1 and in accordance with the general statements on the preparation:

(II)

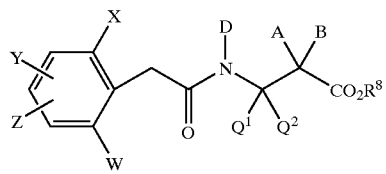

| Ex. No. | W | X | Y | Z | A | B | D | $Q^1$ | $Q^2$ | $R^8$ | m.p. °C. |
|---|---|---|---|---|---|---|---|---|---|---|---|
| II-2 | Cl | Cl | H | H | H | H | —(CH$_2$)$_4$— | | H | C$_2$H$_5$ | 89 |
| II-3 | H | CH$_3$ | 5-Br | H | H | H | H | CH$_3$ | CH$_3$ | C$_2$H$_5$ | 101 |
| II-4 | CH$_3$ | Cl | 4-Cl | H | H | H | H | CH$_3$ | CH$_3$ | C$_2$H$_5$ | 87 |
| II-5 | H | CH$_3$ | 5-(4-Cl—C$_6$H$_4$) | H | H | H | H | CH$_3$ | CH$_3$ | C$_2$H$_5$ | 94 |
| II-6 | CH$_3$ | Cl | 4-Br | H | H | H | H | CH$_3$ | CH$_3$ | C$_2$H$_5$ | 118 |
| II-7 | C$_2$H$_5$ | Cl | 4-Br | H | H | H | H | CH$_3$ | CH$_3$ | C$_2$H$_5$ | 113 |
| II-8 | H | CH$_3$ | 5-(4-Cl—C$_6$H$_4$) | H | CH$_3$ | CH$_3$ | H | H | H | C$_2$H$_5$ | 97 |
| II-9 | H | CH$_3$ | 4-(4-Cl—C$_6$H$_4$) | H | CH$_3$ | CH$_3$ | H | H | H | C$_2$H$_5$ | 123 |
| II-10 | CH$_3$ | Cl | 4-Cl | H | CH$_3$ | CH$_3$ | H | H | H | C$_2$H$_5$ | 114 |
| II-11 | CH$_3$ | CH$_3$ | 3-CH$_3$ | 4-CH$_3$ | CH$_3$ | CH$_3$ | H | H | H | C$_2$H$_5$ | 124 |
| II-12 | CH$_3$ | CH$_3$ | 4-CH$_3$ | H | CH$_3$ | CH$_3$ | H | H | H | C$_2$H$_5$ | 123 |
| II-13 | CH$_3$ | CH$_3$ | 4-CH$_3$ | H | —(CH$_2$)$_5$— | | H | H | H | C$_2$H$_5$ | 126 |
| II-14 | CH$_3$ | CH$_3$ | 3-CH$_3$ | 4-CH$_3$ | —(CH$_2$)$_5$— | | H | H | H | C$_2$H$_5$ | 146 |
| II-15 | CH$_3$ | Cl | 4-Cl | H | —(CH$_2$)$_5$— | | H | H | H | C$_2$H$_5$ | 123 |
| II-16 | H | CH$_3$ | 5-(4-Cl—C$_6$H$_4$) | H | —(CH$_2$)$_5$— | | H | H | H | C$_2$H$_5$ | 120 |
| II-17 | CH$_3$ | CH$_3$ | 4-(4-Cl—C$_6$H$_4$) | H | —(CH$_2$)$_5$— | | H | H | H | C$_2$H$_5$ | 150 |
| II-18 | H | Cl | 4-Cl | H | H | H | —(CH$_2$)$_4$— | | H | C$_2$H$_5$ | oil |
| II-19 | H | CH$_3$ | 5-(4-Cl—C$_6$H$_4$) | H | H | H | —(CH$_2$)$_4$— | | H | C$_2$H$_5$ | oil |
| II-20 | CH$_3$ | CH$_3$ | 4-(4-Cl—C$_6$H$_4$) | H | H | H | —(CH$_2$)$_4$— | | H | C$_2$H$_5$ | 115 |
| II-21 | CH$_3$ | Cl | 4-Cl | H | H | H | ▷ | CH$_3$ | CH$_3$ | C$_2$H$_5$ | oil |
| II-22 | H | CH$_3$ | 5-(4-Cl—C$_6$H$_4$) | H | H | H | ▷ | CH$_3$ | CH$_3$ | C$_2$H$_5$ | oil |
| II-23 | H | CH$_3$ | 5-(4-Cl—C$_6$H$_4$) | H | H | H | CH$_3$ | CH$_3$ | CH$_3$ | C$_2$H$_5$ | oil |
| II-24 | Cl | C$_2$H$_5$ | 4-Br | H | H | H | CH$_3$ | CH$_3$ | CH$_3$ | C$_2$H$_5$ | oil |
| II-25 | CH$_3$ | CH$_3$ | 6-CH$_3$ | H | H | H | CH$_3$ | CH$_3$ | CH$_3$ | C$_2$H$_5$ | oil |
| II-26 | CH$_3$ | Cl | 4-Cl | H | —(CH$_2$)$_2$—O—(CH$_2$)$_2$— | | H | H | H | C$_2$H$_5$ | 121 |
| II-27 | CH$_3$ | CH$_3$ | 4-Cl | H | —(CH$_2$)$_2$—O—(CH$_2$)$_2$— | | H | H | H | C$_2$H$_5$ | 126 |

TABLE 3-continued

The following compounds of the formula (II) are obtained analogously to Example II-1 and in accordance with the general statements on the preparation:

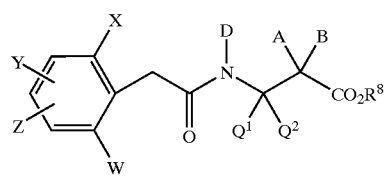

(II)

| Ex. No. | W | X | Y | Z | A | B | D | $Q^1$ | $Q^2$ | $R^8$ | m.p. °C. |
|---|---|---|---|---|---|---|---|---|---|---|---|
| II-28 | $CH_3$ | Cl | 4-Cl | H | H | H | H | $-(CH_2)_2-O-(CH_2)_2-$ | | $C_2H_5$ | 117 |
| II-29 | $CH_3$ | $CH_3$ | 4-Cl | H | H | H | H | $-(CH_2)_2-O-(CH_2)_2-$ | | $C_2H_5$ | 117 |
| II-30 | H | $CH_3$ | 5-(4-Cl—$C_6H_4$) | H | H | H | H | $-(CH_2)_2-O-(CH_2)_2-$ | | $C_2H_5$ | 118 |
| II-31 | $CH_3$ | Cl | 4-(4-Cl—$C_6H_5$) | H | H | H | H | $CH_3$ | $CH_3$ | $C_2H_5$ | 99 |
| II-32 | $C_2H_5$ | Cl | 4-(4-Cl—$C_6H_5$) | H | H | H | H | $CH_3$ | $CH_3$ | $C_2H_5$ | oil |
| II-33 | $CH_3$ | Cl | 4-Cl | H | H | H | H | $-(CH_2)_2-CHOCH_3-(CH_2)_2-$ | | $C_2H_5$ | 113 |
| II-34 | $C_2H_5$ | Cl | 4-Br | H | $-(CH_2)_2-O-(CH_2)_2-$ | | H | H | H | $C_2H_5$ | 139 |
| II-35 | H | $CH_3$ | 5-(4-Cl—$C_6H_4$) | H | H | H | H | $-(CH_2)_2-CHOCH_3-(CH_2)_2-$ | | $C_2H_5$ | 124 |
| II-36 | $C_2H_5$ | Cl | 5-Br | H | H | H | H | $-(CH_2)_2-CHOCH_3-(CH_2)_2-$ | | $C_2H_5$ | 115 |

Use examples

Example A

Meloidogyne Test

| Solvent: | 30 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with water to the desired concentration.

Containers are filled with sand, solution of active compound, Meloidogyne incognita egg/larvae suspension and lettuce seeds. The lettuce seeds germinate and the plants develop. On the roots, galls are formed.

After the desired period of time, the nematicidal action in % is determined using the formation of galls as a measure. 100% means that no galls have been found; 0% means that the number of galls on the treated plants corresponds to that on the untreated control.

In this test, the compound of Preparation Example I-a-4 exhibited, at an exemplary active compound concentration of 20 ppm, a kill of 95% after 14 days.

Example B

Tetranychus Test (OP-Resistent/Dip Treatment)

| Solvent: | 30 parts by weight of dimethylformamide |
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Bean plants (*Phaseolus vulgaris*) which are heavily infested by all stages of the greenhouse rat spider mite (*Tetranychus urticae*) are treated by being dipped into a preparation of active compound of the desired concentration.

After the desired period of time, the effect in % is determined. 100% means that all spider mites have been killed; 0% means that none of the spider mites have been killed.

In this test, for example, compounds of Preparation Examples I-a-5 and I-c-1 exhibit, at an exemplary active compound concentration of 100 ppm, a kill of 99% (I-a-5) and 95% (I-c-1), respectively, after 7 days.

Example C

Post-Emergence Test

| Solvent: | 5 parts by weight of acetone |
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants of a height of 5–15 cm are sprayed with the preparation of active compound such that the particular amounts of active compound desired are applied per unit area. The concentration of the spray liquor was chosen such that the particular amounts of active compound desired are applied in 1000 l of water/ha.

After three weeks, the degree of damage to the plants is rated in % damage in comparison to the development of the untreated control.

The figures denote:

0%=no effect (like untreated control)

100%=total destruction

Example D

Pre-Emergence Test

| Solvent: | 5 parts by weight of acetone |
|---|---|
| Emulsifier: | 1 part by weight of alkylaryl polyglycol ether |

To produce a suitable preparation of active compound, 1 part by weight of active compound is mixed to the stated amount of solvent, the stated amount of emulsifier is added and the concentrate is diluted with water to the desired concentration.

Seeds of the test plants are sown in normal soil. After about 24 hours, the soil is sprayed with the preparation of active compounds such that the particular amounts of active compound desired are applied per unit area. The concentration of the spray liquor is chosen such that the particular amounts of active compound desired are applied in 1000 l of water/ha.

After three weeks, the degree of damage to the plants is rated in % damage in comparison to the development of the untreated control.

The figures denote:

0%=no effect (like untreated control)

100%=total destruction

| Post-emergence/ Greenhouse | g/ha | Sugar beet | Alopecurus | Echinochloa | Setaria | Amaranthus |
|---|---|---|---|---|---|---|
| Ex. I-a-10 | 2000 | 0 | 70 | 80 | 80 | 70 |

| Post-emergence/ Greenhouse | g/ha | Wheat | Soya | Digitaria | Echinochloa | Lolium | Setaria |
|---|---|---|---|---|---|---|---|
| Ex. I-a-10 | 250 | 0 | 0 | 90 | 80 | 100 | 95 |

| Post-emergence/ Greenhouse | g/ha | Sugar beet | Alopecurus | Avena fatua | Echinochloa | Setaria |
|---|---|---|---|---|---|---|
| Ex. I-a-11 | 2000 | 90 | 95 | 100 | 100 | 100 |

| Pre-emergence/ Greenhouse | g/ha | Alopecurus | Avena fatua | Ecbinochloa | Setaria |
|---|---|---|---|---|---|
| Ex. I-a-11 | 2000 | 100 | 100 | 100 | 100 |

| Post-emergence/ Greenhouse | g/ha | Sugar beet | Echinochloa | Setaria | Amaranthus |
|---|---|---|---|---|---|
| Ex. I-c-1 | 250 | 0 | 70 | 80 | 80 |

| Pre-emergence/ Greenhouse | g/ha | Alopecurus | Amaranthus | Galium |
|---|---|---|---|---|
| Ex. I-a-3 | 500 | 70 | 70 | 100 |

Example E

Critical Concentration Test/Soil Insects—Treatment of Transgenic Plants

Test Insect: *Diabrotica Balteata*—Larvae in Soil

| Solvent: | 7 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of the active compound in the preparation is virtually irrelevant, only the amount by weight of active compound per volume unit of soil, which is stated in ppm (mg/l) matters. The soil is filled into 0.25 l pots and these are allowed to stand at 20° C.

Immediately after preparation, 5 pre-germinated maize corns of the variety YIELD GUARD (trade mark of Monsanto Comp., USA) are placed into each pot. After 2 days, the test insects are placed into the treated soil. After a further 7 days, the efficacy of the active compound is determined by counting the maize plants that have emerged (1 plant=20% efficacy).

Example F

*Heliothis Virescens* Test—Treatment of Transgenic Plants

| Solvent: | 7 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Soya bean shoots (Glycine max) of the variety Roundup Ready (trade mark of Monsanto Comp. USA) are treated by being dipped into the preparation of active compound of the desired concentration and are populated with the tobacco budworm *Heliothis virescens* while the leaves are still moist.

After the desired period of time, the kill of the insects is determined.

What is claimed is:

1. A compound of the formula (I)

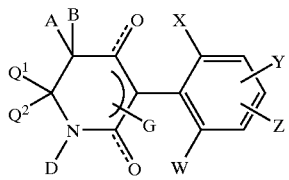
(I)

in which

W represents hydrogen, $C_1$–$C_6$-alkyl, fluorine, chlorine, or bromine;

X represents fluorine; chlorine; bromine; or $C_1$–$C_6$-alkyl;

Y represents hydrogen; $C_1$–$C_6$-alkyl; fluorine; chlorine; bromine; or the radical

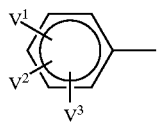
, in which $V^1$ represents hydrogen; halogen; $C_1$–$C_{12}$-alkyl; $C_1$–$C_6$-alkoxy; $C_1$–$C_6$-alkylthio; nitro; or cyano;

$V^2$ represents hydrogen, fluorine, chlorine, or $C_1$–$C_6$-alkyl; and $V^3$ represents hydrogen, fluorine, chlorine, methyl, or ethoxy;

Z represents hydrogen, or $C_1$–$C_6$-alkyl,

A represents hydrogen; or $C_1$–$C_{12}$-alkyl;

B represents hydrogen or $C_1$–$C_6$-alkyl;

D represents hydrogen;

$Q^1$ represents hydrogen; or $C_1$–$C_6$-alkyl;

$Q^2$ represents hydrogen or $C_1$–$C_4$-alkyl; and

G represents hydrogen (a) or the group

(b)

in which $R^1$ represents $C_1$–$C_{20}$-alkyl.

2. A compound of the formula (I)

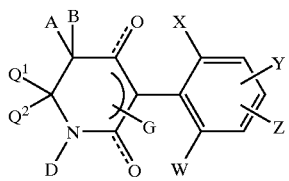
(I)

in which

W represents hydrogen or alkyl;

X represents halogen or alkyl;

Y represents chlorine, bromine, or the radical

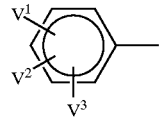
, in which $V^1$ represents hydrogen, halogen, or $C_1$–$C_{12}$-alkyl;

$V^2$ represents hydrogen, fluorine, or chlorine; and $V^3$ represents hydrogen, fluorine, or chlorine;

Z represents hydrogen or $C_1$–$C_6$-alkyl;

A represents hydrogen or $C_1$–$C_{12}$-alkyl;

B represents hydrogen or $C_1$–$C_6$-alkyl;

D represents hydrogen;

$Q^1$ represents hydrogen or $C_1$–$C_6$-alkyl;

$Q^2$ represents hydrogen or $C_1$–$C_4$-alkyl; and

G represents hydrogen (a) or the group

(b)

in which $R^1$ represents $C_1$–$C_{20}$-alkyl.

3. A compound of the formula (I-a)

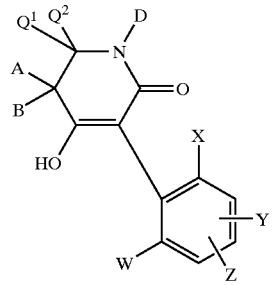
(I-a)

in which

W represents hydrogen, methyl, or ethyl;

X represents chlorine or methyl;

Y represents chlorine, bromine, or the radical

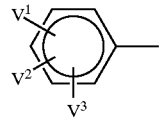
, in which $V^1$ represents hydrogen, or chlorine;

$V^2$ represents hydrogen or chlorine; and $V^3$ represents hydrogen;

Z represents hydrogen;

A and B represent hydrogen;

D represents hydrogen; and $Q^1$ and $Q^2$ represent methyl.

4. A compound of the formula (I) according to claim 1 in which

W represents hydrogen, $C_1$–$C_4$-alkyl, fluorine, chlorine, or bromine;

X represents fluorine, chlorine, bromine, or $C_1$–$C_4$-alkyl;

Y represents hydrogen, $C_1$–$C_4$-alkyl, fluorine, chlorine, bromine, or the radical

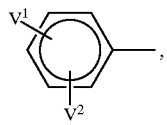

in which

V$^1$ represents hydrogen, fluorine, chlorine, bromine, 1–$C_6$-alkyl, $C_1$–$C_4$-alkoxy, or $C_1$–$C_4$-alkylthio; and V$^2$ represents hydrogen, fluorine, chlorine, or $C_1$–$C_4$-alkyl;

Z represents hydrogen, or $C_1$–$C_4$-alkyl,

A represents hydrogen; or $C_1$–$C_8$-alkyl;

B represents hydrogen or $C_1$–$C_4$-alkyl;

D represents hydrogen:

Q$^1$ represents hydrogen; or $C_1$–$C_4$-alkyl;

Q$^2$ represents hydrogen, methyl or ethyl; and

G represents hydrogen (a) or the group

in which R$^1$ represents $C_1$–$C_{16}$-alkyl.

5. A compound of the formula (I) according to claim 1 in which

W represents hydrogen or $C_1$–$C_4$-alkyl;

X represents fluorine, chlorine, bromine, or $C_1$–$C_4$-alkyl;

Y represents chlorine, bromine, or the radical

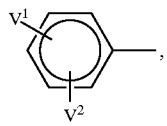

in which

V$^1$ represents hydrogen, fluorine, chlorine, bromine, or $C_1$–$C_6$-alkyl; and V$^2$ represents hydrogen, fluorine, chlorine or $C_1$–$C_4$-alkyl;

Z represents hydrogen or $C_1$–$C_6$-alkyl:

A represents hydrogen or $C_1$–$C_8$-alkyl;

B represents hydrogen or $C_1$–$C_4$-alkyl;

D represents hydrogen;

Q$^1$ represents hydrogen or $C_1$–$C_4$-alkyl;

Q$^2$ represents hydrogen, methyl, or ethyl;

G represents hydrogen (a) or the group

in which R$^1$ represents $C_1$–$C_{16}$-alkyl.

6. A compound of the formula (I) according to claim 1 in which

W represents hydrogen, fluorine, chlorine, bromine, methyl, ethyl, or propyl;

X represents fluorine, chlorine, bromine, methyl, ethyl, n-propyl, or iso-propyl, Y represents hydrogen, methyl, ethyl, propyl, iso-propyl, fluorine, chlorine, bromine, or the radical

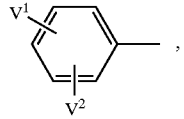

in which

V$^1$ represents hydrogen, fluorine, chlorine, bromine, ethyl, ethyl, n-propyl, iso-propyl, n-butyl, iso-butyl, tert-butyl, methoxy, ethoxy, n-propoxy, or iso-propoxy; and V$^2$ represents hydrogen, fluorine, chlorine, or methyl;

Z represents hydrogen, methyl, or ethyl;

A represents hydrogen, methyl, ethyl, propyl, iso-propyl, butyl, or iso-butyl;

B represents hydrogen, methyl, or ethyl;

D represents hydrogen;

Q$^1$ represents hydrogen, methyl, ethyl, propyl, or iso-propyl;

Q$^2$ represents hydrogen, methyl, or ethyl; and

G represents hydrogen (a) or the group

in which R$^1$ represents $C_1$–$C_{14}$-alkyl.

7. A compound of the formula (I) according to claim 1 in which

W represents hydrogen, methyl, ethyl, or propyl;

X represents fluorine, chlorine, bromine, methyl, ethyl, n-propyl, or isopropyl, Y represents chlorine, bromine, or the radical

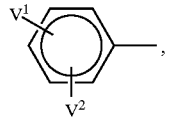

in which

V$^1$ represents hydrogen, fluorine, chlorine, bromine, methyl, ethyl, n-propyl, iso-propyl, n-butyl, isobutyl, or tert-butyl; and V$^2$ represents hydrogen, fluorine, chlorine, or methyl;

Z represents hydrogen, methyl, or ethyl;

A represents hydrogen, methyl, ethyl, propyl, isopropyl, butyl, or iso-butyl;

B represents hydrogen, methyl, or ethyl;

D represents hydrogen;

$Q^1$ represents hydrogen, methyl, ethyl, propyl, or isopropyl;

$Q^2$ represents hydrogen, methyl, or ethyl;

G represents hydrogen (a) or the group

(b)

in which $R^1$ represents $C_1$–$C_{14}$-alkyl.

8. A compound of the formula (I) according to claim 1 in which

W represents hydrogen, fluorine, chlorine, bromine, methyl, or ethyl;

X represents chlorine, bromine, methyl, ethyl, propyl;

Y represents hydrogen, chlorine, bromine, fluorine, methyl, ethyl, or the radical

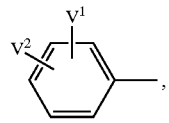, in which $V^1$ represents hydrogen, fluorine, chlorine, bromine, ethyl, or tert-butyl; and $V^2$ represents hydrogen, fluorine, chlorine, or methyl;

Z represents hydrogen, or methyl;

A represents methyl, ethyl, or propyl;

B represents methyl or ethyl;

D represents hydrogen;

$Q^1$ and $Q^2$ represent hydrogen; and

G represents hydrogen (a) or the group

(b)

in which $R^1$ represents $C_1$–$C_8$-alkyl.

9. A compound of the formula (I) according to claim 1 in which

W represents hydrogen, methyl, or ethyl;

X represents chlorine, bromine, methyl, ethyl, or propyl,

Y represents chlorine, bromine, or the radical

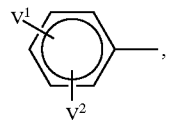, in which $V^1$ represents hydrogen, fluorine, chlorine, bromine, ethyl, or tert-butyl; and $V^2$ represents hydrogen, fluorine, chlorine, or methyl;

Z represents hydrogen or methyl;

A represents methyl, ethyl, or propyl;

B represents methyl or ethyl;

D represents hydrogen;

$Q^1$ and $Q^2$ represent hydrogen; and

G represents hydrogen (a) or the group

(b)

in which $R^1$ represents $C_1$–$C_8$-alkyl.

10. A compound of the formula (I) according to claim 1 in which

W represents hydrogen, fluorine, chlorine, bromine, methyl, or ethyl;

X represents chlorine, bromine, methyl, ethyl, or propyl;

Y represents hydrogen, methyl, ethyl, fluorine, chlorine, bromine, or the radical

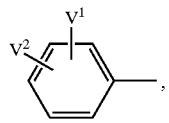, in which $V^1$ represents hydrogen, fluorine, chlorine, bromine, methyl, or tert-butyl; and $V^2$ represents hydrogen, fluorine, chlorine, or methyl;

Z represents hydrogen, or methyl;

A and B represent hydrogen;

D represents hydrogen;

$Q^1$ represents methyl, ethyl, or propyl;

$Q^2$ represents methyl; and

G represents hydrogen (a) or the group

(b)

in which $R^1$ represents $C_1$–$C_8$-alkyl.

11. A compound of the formula (I) according to claim 1 in which

W represents hydrogen, methyl, or ethyl;

X represents chlorine, bromine, methyl, ethyl, or propyl,

Y represents chlorine, bromine, or the radical

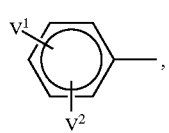, in which $V^1$ represents hydrogen, fluorine, chlorine, bromine, methyl, or tert-butyl; and $V^2$ represents hydrogen, fluorine, chlorine, or methyl;

Z represents hydrogen or methyl;

A and B represent hydrogen;

D represents hydrogen;

$Q^1$ represents methyl, ethyl, or propyl;

$Q^2$ represents methyl; and

G represents hydrogen (a) or the group (b)

in which $R^1$ represents $C_1$–$C_8$-alkyl.

12. A compound of the formula (I-a)

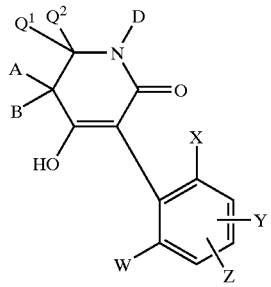

(I-a)

in which
W, Z, A, B, and D represent hydrogen;
X, $Q^1$, and $Q^2$ represent methyl; and
Y represents 5-(4-Cl—$C_6H_5$).

13. An insecticide or acaricide composition comprising one or more compounds of the formula (I) according to claim 1 and an inert carrier.

14. A method for controlling undesirable insects, arachnids, or mites comprising allowing an effective amount of a compound of the formula (I) according to claim 1 to act on an undesirable insect, arachnid, or mite and/or the habitat of an undesirable insect, arachnid, or mite.

* * * * *